US006903117B2

(12) United States Patent  
Farina et al.

(10) Patent No.: US 6,903,117 B2  
(45) Date of Patent: *Jun. 7, 2005

(54) INDOLE DERIVATIVES FOR THE TREATMENT OF OSTEOPOROSIS

(75) Inventors: Carlo Farina, Milan (IT); Stefania Gagliardi, Milan (IT); Guy Marguerite Marie Gerard Nadler, Rennes (FR)

(73) Assignee: Nikem Research S.R.L., Milan (IT)

( * ) Notice: Subject to any disclaimer, the term of this patent is extended or adjusted under 35 U.S.C. 154(b) by 127 days.

This patent is subject to a terminal disclaimer.

(21) Appl. No.: 10/300,332

(22) Filed: Nov. 20, 2002

(65) Prior Publication Data

US 2004/0010012 A1 Jan. 15, 2004

Related U.S. Application Data

(63) Continuation of application No. 10/005,491, filed on Dec. 4, 2001, now abandoned, which is a continuation of application No. 09/704,410, filed on Nov. 2, 2000, now abandoned, which is a continuation of application No. 09/214,692, filed as application No. PCT/EP97/03577 on Jul. 3, 1997, now abandoned.

(30) Foreign Application Priority Data

Jul. 9, 1996 (GB) .............................. 9614367  
Dec. 23, 1996 (GB) .............................. 9626697  
Dec. 23, 1996 (GB) .............................. 9626700

(51) Int. Cl.[7] ..................... A61K 31/454; C07D 401/12  
(52) U.S. Cl. ..................... 514/323; 546/201; 546/256; 546/277.4; 546/112; 544/316; 544/373; 548/312.1; 548/491; 514/253; 514/274; 514/299; 514/333; 514/339; 514/397; 514/419  
(58) Field of Search ............................ 514/323, 419, 514/339, 299, 274, 253; 546/201, 256, 277.4, 112; 544/316, 373; 548/312.1, 491

(56) References Cited

U.S. PATENT DOCUMENTS 5,296,499 A    3/1994  Sohda et al.  
5,981,525 A   11/1999  Farina et al. ............. 514/235.2

FOREIGN PATENT DOCUMENTS

WO    WO 93/01280    1/1993  
WO    WO 96/21644    7/1996

OTHER PUBLICATIONS

Tsuda, et al., Chemical Abstracts, vol. 123, No. 23, 1995, abstract No. 306604k, p. 96.

Primary Examiner—Charanjit S. Aulakh  
(74) Attorney, Agent, or Firm—Wolf, Greenfield & Sacks, P.C.

(57) ABSTRACT

A compound of formula (I):

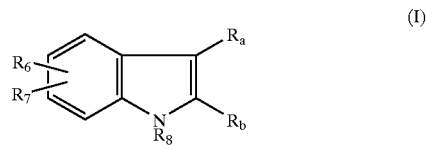

or a salt thereof, or a solvate thereof, wherein Ra represents a group $R_5$ which is hydrogen, alkyl or optionally substituted aryl and Rb represents a moiety of formula (a):

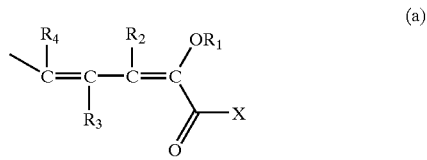

wherein X represents a hydroxy or an alkoxy group wherein the alkyl group may be substitued or unsubstituted or X represents a group $NR_sR_t$ wherein $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together with the nitrogen to which they are attached form a heterocyclic group; $R_1$ represents an alkyl or a substituted or unsubstituted aryl group; and $R_2$, $R_3$ and $R_4$ each independently represent hydrogen, alkyl, aryl or substituted aryl; $R_6$ and $R_7$ each independently represent hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino; and $R_8$ represents hydrogen, hydroxy, alkynoyl, alkyl, aminoalkyl, hydroxyalkyl, carboxyalky, carbalkoxyalkyl, carbamoyl or aminosulphonyl; a process for preparing such a compound, a pharmaceutical composition containing such a compound and the use of such a compound in medicine.

4 Claims, No Drawings

INDOLE DERIVATIVES FOR THE TREATMENT OF OSTEOPOROSIS

This is a continuation of application Ser. No: 10/005,491 filed Dec. 4, 2001 now abandoned which is a continuation of 09/704,410 filed Nov. 2, 2000 now abandoned which is a continuation of 09/214,692 filed Jan. 8, 1999, now abandoned which is a 371 of International Application No. PCT/EP97/03577 filed Jul. 3, 1997, which claims benefit of GB applications, 9626700.0 filed Dec. 23, 1996, 9626697.8 filed Dec. 23, 1996 and 9614367.2 filed Jul. 9, 1996.

This invention relates to certain novel compounds, to a process for preparing such compounds, to pharmaceutical compositions containing such compounds and to the use of such compounds and compositions in medicine.

Co-pending International Application, application number PCT/EP96/00157, publication number WO 96/21644, discloses certain indole derivatives of formula (A): formula (I):

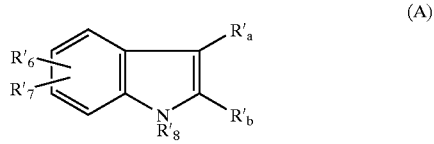

(A)

or a salt thereof, or a solvate thereof, wherein either: (i) R'a represents a group R'$_5$ which is hydrogen, alkyl or optionally substituted aryl and R'b represents a moiety of formula (a'):

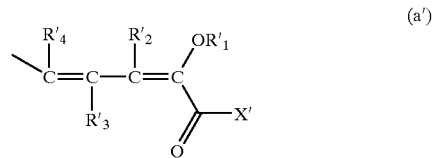

(a')

wherein X' represents a hydroxy or an alkoxy group wherein the alkyl group may be substituted or unsubstituted or X' represents a group NR'$_s$R'$_t$ wherein R'$_s$ and R'$_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or R'$_s$ and R'$_t$ together with the nitrogen to which they are attached form a heterocyclic group; R'$_1$ represents an alkyl or a substituted or unsubstituted aryl group; and R'$_2$, R'$_3$ and R'$_4$ each independently represent hydrogen, alkyl, aryl or substituted aryl or (ii) R'$_a$ represents a moiety of the above defined formula (a) and R'$_b$ represents the above defined R'$_5$;

R'$_6$ and R'$_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or R'$_6$ and R'$_7$ together represent methylenedioxy, carbonyldioxy or carbonyldiamino; and R'$_8$ represents hydrogen, hydroxy, alkanoyl, alkyl, aminoalkyl, hydroxyalkyl, carboxyalkyl, carbalkoxyalkyl, carbamoyl or aminosulphonyl, which compounds are indicated interalia to reduce bone resorption by inhibiting osteoclast H$^+$-ATPase.

Diseases associated with loss of bone mass are known to be caused by over activity of osteoclast cells. It is also known that certain compounds, usually related to bafilomycin, are useful for treating such diseases: For example International Patent Application, publication number WO 91/06296 discloses certain bafilomycin macrolides for the treatment of bone affecting diseases.

However, bafilomycin derivatives are not selective for osteoclasts in humans. The use of these compounds is therefore associated with unacceptable toxicity due to generalised blockade of other essential v-ATPases. Indeed, to date there is no known treatment which is selective for the human osteoclasts.

The search for a successful treatment for diseases associated with loss of bone mass in humans is further complicated in that the nature of the therapeutic target for the selective inhibition of the osteoclasts is controversial. Thus Baron et al (International Patent Application publication number WO93/01280) indicate that a specific vacuolar ATPase (V-ATPase) has been identified in osteoclasts as a potential therapeutic target. However, the Baron work was carried out in chickens and Hall et al (Bone and Mineral 27, 1994, 159–166), in a study relating to mammals, conclude that in contrast to avian osteoclast V-ATPase, mammalian osteoclast V-ATPase is pharmacologically similar to the v-ATPase in other cells and, therefore, it is unlikely to be a good therapeutic target.

We have now found a group of novel compounds from within the scope of WO 96/21644 which are especially selective for mammalian osteoclasts, especially human osteoclasts, acting to selectively inhibit their bone resorbing activity. These compounds are therefore considered to be particularly useful for the treatment and/or prophylaxis of diseases associated with loss of bone mass, such as osteoporosis and related osteopenic diseases, Paget's disease, hyperparathyroidism and related diseases. These compounds are also considered to possess anti-tumour activity, antiviral activity (for example against Semliki Forest, Vesicular Stomatitis, Newcastle Disease, Influenza A and B, HIV viruses), antiulcer activity (for example the compounds may be useful for the treatment of chronic gastritis and peptic ulcer induced by *Helicobacter pylori*), immunosupressant activity, antilipidemic activity, antiatherosclerotic activity and to be useful for the treatment of AIDS and Alzheimer's disease. In a further aspect, these compounds are also considered useful in inhibiting angiogenesis, i.e. the formation of new blood vessels which is observed in various types of pathological conditions (angiogenic diseases) such as rheumatoid arthritis, diabetic retinopathy, psoriasis and solid tumours Accordingly, in its broadest aspect the the present invention provides a selective inhibitor of the biological activity of human osteoclast cells, in particular the bone resorption activity of human osteoclast cells associated with abnormal loss of bone mass, providing that such an inhibitor does not include any specific Example disclosed in WO 96/21644. In a further aspect the invention provides a selective inhibitor of the biological activity of human osteoclast cells, in particular the bone resorption activity of human osteoclast cells associated with abnormal loss of bone mass, providing that such an inhibitor does not include a compound of the hereinbefore defined compound of formula (A). A particular inhibitor of human osteoclast cells is a selective inhibitor of the vacuolar H$^+$-ATPase located on the ruffled border of human osteoclasts.

In one particular aspect the selective inhibitor interacts specifically with the 16 kDa subunit of the vacuolar H+-ATPase located on the ruffled border of human osteoclasts whose function and structure is similar to other known 16 kDa subunits, for example that reported in P. C. Jones et al., Membrane Dynamics and Transport, 22, 805–809 (1994).

In a further particular aspect, the selective inhibitor interacts specifically with the 116 kDa subunit of the vacuolar H+-ATPase located on the ruffled border of human osteoclasts (for example the protein reported in Y-P. Li et al., Biochem. Biophys. Res. Commun, 218, 813–821 (1996)).

In particular, the invention provides a compound of formula (I):

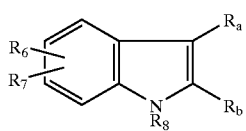

(I)

or a salt thereof, or a solvate thereof, wherein

Ra represents a group $R_5$ which is hydrogen, alkyl or optionally substituted aryl and Rb represents a moiety of formula (a):

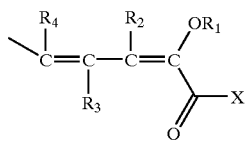

(a)

wherein X represents a hydroxy or an alkoxy group wherein the alkyl group may be substituted or unsubstituted or X represents a group $NR_sR_t$ wherein $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_s$ and $R_t$ together with the nitrogen to which they are attached form a heterocyclic group; $R_1$ represents an alkyl or a substituted or unsubstituted aryl group; and $R_2$, $R_3$ and $R_4$ each independently represent hydrogen, alkyl, aryl or substituted aryl $R_6$ and $R_7$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_6$ and $R_7$ together represent methylenedioxy, carbonyldioxy or carbonyldiamino; and $R_8$ represents hydrogen, hydroxy, alkanoyl, alkyl, aminoalkyl, hydroxyalkyl, carboxyalkyl, carbalkoxyalkyl, carbamoyl or aminosulphonyl.

In one aspect $R_1$ represents alkyl or substituted or unsubstituted phenyl.

Suitably $R_1$ represents alkyl.

Favourably, $R_1$ represents a $C_{1-4}$-alkyl group, for example methyl or ethyl Preferably, $R_1$ represents methyl.

In one aspect, $R_2$, $R_3$ and $R_4$ each independently represent hydrogen, alkyl or phenyl.

Examples of $R_2$ include hydrogen and methyl.

Suitably, $R_2$ represents hydrogen.

Examples of $R_3$ include hydrogen and methyl or ethyl.

Suitably, $R_3$ represents hydrogen.

Examples of $R_4$ include hydrogen, propyl and phenyl, especially hydrogen and phenyl.

Suitably, $R_4$ represents hydrogen.

In one aspect, $R_5$ is hydrogen, alkyl or substituted or, suitably, unsubstituted phenyl.

Examples of $R_5$ include hydrogen, ethyl and 4-methoxyphenyl, especially hydrogen and ethyl.

Suitably, $R_5$ is hydrogen.

In one aspect $R_6$ and $R_7$ each independently represents hydrogen, hydroxy, amino, alkoxy, optionally substituted phenyloxy, optionally substituted benzyloxy, alkylamino, dialkylamino, halo, trifluoromethyl, nitro, alkyl, carboxy, carbalkoxy, carbamoyl, alkylcarbamoyl, or $R_6$ and $R_7$ together represent methylenedioxy, carbonyldioxy or carbonyldiamino.

Suitably, $R_6$ and $R_7$ each independently represents alkoxy, halo, trifluoromethyl, nitro, and alkyl.

When $R_6$ or $R_7$ represents alkoxy, said alkoxy group is suitably a $C_{1-6}$ alkoxy for example methoxy.

When $R_6$ or $R_7$ represents halo, said halo group is suitably a fluoro, chloro or bromo group, especially a chloro or bromo group.

When $R_6$ or $R_7$ represents alkyl, said alkyl group is suitably a $C_{1-6}$ alkyl for a example butyl group.

Suitable positions for substitution for $R_6$ or $R_7$ are the 4, 5, 6 or 7 position, favourably the 5 or 6 position.

When neither of $R_6$ or $R_7$ represent hydrogen then favoured positions for bis-substitution are 5 and 6 positions.

Favoured values for $R_6$ and $R_7$ are hydrogen, halo, trifluoromethyl and alkoxy.

In one aspect $R_6$ is hydrogen and $R_6$ or $R_7$ represents hydrogen alkoxy, halo, nitro, trifluoromethyl and alkyl.

In a further aspect $R_6$ and $R_7$ are each selected from hydrogen, halo and alkoxy, examples include: $R_6$ is halo and $R_7$ is halo; $R_6$ is halo and $R_7$ is alkyl; $R_6$ is alkoxy and $R_7$ is alkoxy.

In a preferred aspect $R_6$ is halo, especially 5-halo, and $R_7$ is halo, especially 6-halo.

Most preferably $R_6$ is chloro, especially 5-chloro, and $R_7$ is chloro, especially 6-chloro.

Examples of $R_8$ include hydrogen, methyl and t-butoxycarbonylmethyl.

A further example of $R_8$ is a carboxymethyl group.

Suitably, $R_8$ represents hydrogen.

When X represents an alkoxy group, the alkyl group thereof is preferably an unsubstituted alkyl group.

Suitably, X represents the above defined group N $R_s$ $R_t$.

In one aspect, $R_s$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group.

$R_s$ and $R_t$ can also each independently represent cycloalkyl or substituted cycloalkyl.

In a further aspect, $R_s$ and $R_t$ together represent a heterocyclic group.

When $R_s$ or $R_t$ represent alkyl or substituted alkyl, suitable alkyl groups are $C_{1-6}$ alkyl groups, for example $C_1$, $C_2$, $C_3$, $C_4$ and $C_5$ alkyl groups, favourably ethyl, propyl or butyl.

When $R_s$ or $R_t$ represent substituted alkyl, favoured groups are 2-(dialkylamino)ethyl or 3-(dialkylamino)propyl or 4-(dialkylamino)butyl or heterocyclylmethyl or heterocyclylethyl or heterocyclylpropyl groups.

A further favoured group for $R_s$ or $R_t$ is heterocyclylalkyl, especially heterocyclyl-$C_{1-6}$ alkyl, in particular heterocyclyl-$(CH_2)_2$— or heterocyclyl-$(CH_2)_3$—.

One favoured heterocyclyl substituent for alkyl groups, such as heterocyclylmethyl, heterocyclylethyl or heterocyclylpropyl groups include piperazinyl groups.

Further favoured heterocyclyl substituents for alkyl groups, such as heterocyclylmethyl, heterocyclylethyl or heterocyclylpropyl groups include homopiperazinyl groups.

When $R_s$ or $R_t$ represent cycloalkyl or substituted cycloalkyl, suitable cycloalkyl groups are $C_{5-9}$ cycloalkyl groups, for example a cyclopentyl or cyclohexyl group. When $R_s$ or $R_t$ represent alkenyl or substituted alkenyl, suitable alkenyl groups are $C_{2-6}$ alkenyl groups, for example a $C_5$ alkenyl group.

When $R_s$ or $R_t$ represent aryl or substituted aryl, suitable aryl groups are phenyl groups.

In one favoured aspect $R_t$ is hydrogen.

Suitable heterocyclic groups include single ring saturated heterocyclic groups, single ring unsaturated heterocyclic groups, fused ring heterocyclic groups.

Fused ring heterocyclic groups include spiro heterocyclic groups.

Suitable single ring unsaturated heterocyclic groups comprise 5-, 6- or 7-membered rings.

Suitable 5-membered single ring unsaturated heterocyclic groups are furanyl, thienyl, pyrrolyl, pyrazolyl, imidazolyl, triazolyl, tetrazolyl, oxazolyl, isoxazolyl, furazanyl, thiazolyl and isothiazolyl groups; or partially saturated derivatives thereof, such as 4,5-dihydro-1,3-thiazol-2-yl, 1H-imidazolinyl, pyrrolinyl, pyrazolinyl, oxazolinyl, isoxazolinyl, thiazolinyl groups.

Suitable 6-membered single ring unsaturated heterocyclic groups are pyridyl, pyrimidinyl, pyridazinyl, pyrazinyl, triazinyl, tetrazinyl, 1,2- or 1,3- or 1,4-oxazinyl, 1,2- or 1,3- or 1,4-thiazinyl and pyranyl groups, or partially saturated derivatives thereof such as 1,2- or 1,3- or 1,4-dihydrooxazinyl, 1,4-dihydropyridyl, dihydropyridazinyl, dihydropyrazinyl or dihydropyrimidinyl.

A further suitable 6-membered single ring unsaturated heterocyclic group is a pyridin-2-one-5-yl group.

Suitable 7-membered single ring unsaturated heterocyclic groups are azepinyl, oxepinyl, diazepinyl, thiazepinyl, oxazepinyl or partially saturated derivatives thereof.

Suitable, single ring saturated heterocyclic groups comprise 5-, 6- or 7-membered rings.

Suitable 5-membered single ring saturated heterocyclic groups are pyrrolidinyl, imidazolidinyl, pyrazolidinyl, oxazolidinyl, isoxazolidinyl and terahydrofuranyl groups.

Suitable 6-membered single ring saturated heterocyclic groups are piperidinyl, piperazinyl, tetrahydropyranyl, 1,3-dioxacyclohexyl, tetrahydro-1,4-thiazinyl, morpholinyl and morpholino groups.

Suitable piperazinyl groups are 1-piperazinyl groups, especially 1-piperazinyl groups substituted in the 4 position with an acyl group, suitably a phenylcarbonyl group, or a heterocyclic group, such as a pyrimidyl group, or an optionally substituted phenyl group, such as a phenyl group with 1, 2, or 3 subsitutents selected from alkoxy and halogen.

Suitable 7-membered single ring saturated heterocyclic groups are hexamethyleniminyl, oxepanyl and thiepanyl.

Suitable fused ring heterocyclic groups include fused saturated rings, fused unsaturated rings and saturated rings fused to unsaturated rings.

Preferred fused ring heterocyclic groups include those comprising two or three rings wherein each ring comprises 4 to 8 ring atoms including 1, 2 or 3, especially 1 or 2, hetero atoms.

Suitable hetero atoms are nitrogen atoms.

Suitable groups having fused saturated rings are polycyclic groups wherein the rings share a single atom, one bond or more than one bond, for example 2 bonds or three bonds. Suitable groups having fused saturated rings are quinuclidyl, 8-azabicyclo[3.2.1]octyl, 9-azabicyclo[3.3.1]nonyl, 1-azabicyclo[3.3.3]undecyl, 1,9-diazabicyclo[3.3.1] and 1,5-diazabicyclo[3.3.1]nonyl groups.

Further suitable groups having fused saturated rings are decahydro-pyrrolo[2.1.5-cd]indolizinyl, octahydroindolizinyl, octahydro-2H-quinolizinyl and tricyclo[3.3.1.1$^{3,7}$]decyl groups.

A further suitable group comprising a fused saturated ring is a nonyl 1-azabicyclo[3.3.1]nonyl, 3,7-diazabicyclo[3.3.1] nonyl group.

Suitable groups having fused unsaturated rings are pyrazo[3.4-d]pyrimidinyl, 1,2,5-thiadiazolo[3,4-b]pyridyl, isoxazolo[4,5-b]pyridyl, thiazolo[4,5-b]pyridyl, oxazolo[4,5-d]pyrimidinyl, 7H-purin-2-yl, quinolyl, isoquinolyl, benzo[b]thienyl, benzofuranyl, isobenzofuranyl, benzoxazolyl, benzothiazolyl, indolizinyl, indolyl, isoindolyl, indazolyl, phthalazinyl, naphthyridinyl, quinoxalinyl, quinazolinyl, cinnolinyl, pteridinyl and β-carbolinyl groups.

Suitable groups having saturated rings fused to unsaturated rings includes groups which are fused to benzene rings such as tetrahydroquinolyl, 4H-quinolizinyl, tetrahydroisoquinolyl, dihydrobenzofuryl, chromenyl, chromanyl, isochromanyl, indolinyl and isoindolinyl groups.

Suitable spiro heterocyclic groups include oxaspiro[4.5]decyl, azaspiro[4.5]decyl, 1,2,4-triazaspiro[5.5]undecyl, 1,4-dioxa-9-azaspiro[4.7]dodecyl and 1-azaspiro[5.5]undecyl.

Suitable values for $R_s$ include hydrogen, $C_{1-5}$ alkyl, mono- di- and tri-hydroxyalkyl, alkoxyalkyl, carboxyalkyl, carbalkoxyalkyl, bisphosphonylalkyl, (substituted)aminocarboxyalkyl, biscarbethoxy-hydroxyalkenyl, dialkylaminoalkylpyridyl, mono- di- and tri-alkoxypyridyl, dialkylaminoalkoxypyridyl, aryloxypyridyl, aminopyridyl, substituted piperazinyl, quinuclidyl, saturated heterocyclylalkyl, substituted piperidinyl, (di)azabicycloalkyl, substituted phenyl, substituted benzyl, substituted phenylethyl, 1-imidazolylalkyl, thiazolinyl, (2-tetrahydroisoquinolinyl)alkyl, 1H-pyrazolo[3,4-d]pyrimidin-4-yl, 7H-purin-2-yl, pyridylalkyl, (2-pyrimidinyl)piperazin-1-ylalkyl, substituted pyridazinyl, substituted pyrazinyl, substituted pyrimidinyl, quinolyl, isoquinolyl, tetrahydroisoquinolyl, tetrahydroquinolyl.

Other suitable values for Rs include, (4-substituted)piperazinoalkyl and aminopyrimidiniyl.

Preferred values for $R_s$ include diethylaminopropyl, 3-amino-3-carboxypropyl, 4-amino-4-carboxybutyl, 3-pyridyl, diethylaminoethyl, 3-quinuclidyl (or 1-azabicyclo[2.2.2]octan-3-yl), morpholinopropyl, piperidinopropyl, 1-methyl-2-pyrrolidinylethyl, 2,2,6,6-tetramethyl-4-piperidinyl, 2-methoxy-5-pyridyl, 2-methylpiperidinopropyl, 8-methyl-8-azabicyclo[3.2.1]oct-3β-yl, 1-methyl-4-piperidinyl, 1H-pyrazolo[3,4-d]pyrimidin-4-yl, 2,2,5,5-tetramethyl-3-pyrrolidinylmethyl, 2-methoxy-4-pyridyl, 1-ethyl-3-piperidinyl, 3-[4-(2-pyrimidinyl)piperazin-1-yl]propyl.

Other preferred values for $R_s$ include dimethylaminopropyl, dibutylaminopropyl, 2-methoxypyrimidin-5-yl, 3-[4-(3-chlorophenyl)piperazin-1-yl]propyl, 3-[4-(2-phenyl)piperazin-1-yl]propyl, 3-[2,6-dimethyl-4-(2-pyrimidinyl)piperazin-1-yl]propyl], 3-dimethylaminocyclohexyl, 1-(2-hydroxyethyl)-2,6-dimethylpiperidin-4-yl, 8a βH-5α-methyl-octahydroindolizin-7α-yl, 3-[4-(2-pyridyl)piperazin-1-yl]propyl, 3-[4-(2-methoxyphenyl)

piperazin-1-yl]propyl and 3-[4-(2-pyrimidinyl)
homopiperazin-1-yl]propyl].

Other preferred values for $R_s$ include 1,2,2,6,6-pentamethyl-4-piperidinyl, 1,2,6-trimethyl-4-piperidinyl and 1,2,2,6-tetramethyl-4-piperidinyl groups.

Suitable values for $R_t$ include hydrogen, methyl, $C_{2-5}$ alkyl, 2-hydroxyethyl, 2-methoxyethyl, carboxymethyl, carbomethoxymethyl, 4-hydroxybutyl and 2,3-dihydroxypropyl, especially hydrogen.

In one preferred aspect $R_t$ represents hydrogen.

A particular 6 membered single ring unsaturated heterocyclic group is a moiety of formula (H1):

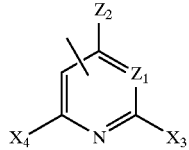

(H1)

wherein $Z_1$ is N or $CX_5$ wherein $X_5$ is selected from hydrogen, alkyl, alkoxy, alkylcarbonyl, aryl, aryloxy or arylcarbonyl and $Z_2$, $X_3$ and $X_4$ are each independently selected from hydrogen, alkyl, aryl, cyano, amino, heterocyclyloxy, alkoxy carbonylalkyloxy, carboxyalkyloxy, aminoalkyloxy, aminoalkylamino, aminoalkenylamino (especially aminomethyleneamino) and alkanoylamino.

A particularly preferred compound of the invention is a compound of formula (I) wherein: $R_a$ is a group $R_5$ wherein $R_5$ is as defined in relation to formula (I); $R_b$ is a moiety of formula (a) wherein $R_1$, $R_2$, $R_3$ and $R_4$ are as defined in relation to formula (I) and X is a moiety $NR_sR_t$ wherein $R_s$ is a group (H1) as defined above, and $R_t$ is hydrogen.

A favoured moiety $NR_sR_t$ is an optionally substituted piperidinyl group, especially wherein one of the substituents is an N-alkyl group.

Particular substituents for piperidinyl groups are alkyl groups, especially when attached to one or, favourably, both of the carbon atoms alpha to the ring nitrogen atom.

Piperidinyl groups of especial interest are those wherein one or, favourably, both of the carbon atoms alpha to the ring nitrogen atom are substitued with one or, favourably, two alkyl groups.

Further particular substituents for piperidinyl groups are alkylene groups, especially when attached to one, favourably both, of the carbon atoms alpha to the ring nitrogen atom.

A particular 6 membered, saturated heterocyclic group is a group of formula (H2):

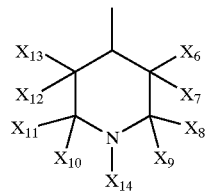

(H2)

wherein $X_6$, $X_7$, $X_8$, $X_9$, $X_{10}$, $X_{11}$, $X_{12}$ and $X_{13}$ are each independently selected from hydrogen, hydroxy, alkyl, suitably $C_{1-6}$ alkyl, cycloalkyl (including spirocondensed), mono or poly hydroxyalkyl, alkoxyalkyl, hydroxy-alkoxyalkyl, alkanoyl, alkoxycarbonyl, aminoalkyl (optionally alkylated or acylated at nitrogen);

or one of $X_6$ with $X_{12}$ and $X_8$ with $X_{10}$ represents a $C_{2-4}$ alkylene chain and the remaining variables $X_7$, $X_{13}$, $X_9$ and $X_{11}$ each independently represent hydrogen, hydroxy, alkyl, suitably $C_{1-6}$ alkyl, cycloalkyl (including spirocondensed), mono or poly hydroxyalkyl, alkoxyalkyl, hydroxy-alkoxyalkyl, alkanoyl, alkoxycarbonyl, aminoalkyl (optionally alkylated or acylated at nitrogen); and $X_{14}$ represents hydrogen or alkyl, especially $C_{1-6}$ alkyl, mono or polyhydroxyalkyl, mono or diaminoalkyl, aminocarbonyl, alkylcarboxyalkyl, carbalkoxyalkyl, aryl, heterocyclyl, acyl, carbamoyl, alkylamino(cyanimidoyl), aminoalkanoyl, hydroxyalkanoyl.

Suitably, $X_6$, $X_7$, $X_{12}$ and $X_{13}$ each represent hydrogen.

Suitably, $X_8$, and $X_9$ each independently represent hydrogen or alkyl, especially alkyl, for example methyl.

Suitably, $X_{10}$ and $X_{11}$ each independently represent hydrogen or alkyl, especially alkyl, for example methyl Suitably, $X_{14}$ represents alkyl, for example methyl In one preferred aspect $X_8$, $X_9$, $X_{10}$ and $X_{11}$ each independently represent alkyl, especially methyl, and $X_6$, $X_7$, $X_{12}$ and $X_{13}$ each represent hydrogen.

In a most preferred aspect $X_8$, $X_9$, $X_{10}$ and $X_{11}$ each independently represent alkyl, especially methyl, and $X_6$, $X_7$, $X_{12}$ and $X_{13}$ each represent hydrogen and $X_{14}$ represents alkyl, especially methyl.

A preferred compound of the invention is a compound of formula (I) wherein $R_a$ is a group $R_5$ wherein $R_5$ is as defined in relation to formula (I); $R_b$ is a moiety of formula (a) wherein $R_1$, $R_2$, $R_3$ and $R_4$ are as defined in relation to formula (I) and X is a moiety $NR_sR_t$ wherein $R_s$ is a moiety of formula (f) defined below, especially a moiety (f) wherein k is zero and $H_0$ is a moiety (a) as defined below, or a moiety (H1) or (H2) as defined above, and $R_t$ is hydrogen, suitably wherein $R_s$ is a moiety of formula (H1) or (H2) and $R_6$, $R_7$ and $R_8$ are as defined in relation to formula (I).

A particularly preferred compound of the invention is a compound at formula (I) wherein $R_a$ is a group $R_5$ wherein $R_5$ is as defined in relation to formula (I); $R_b$ is a moiety of formula (a) wherein $R_1$, $R_2$, $R_3$ and $R_4$ are as defined in relation to formula (I) and X is a moiety $NR_sR_t$ wherein $R_s$ is a group (H2), as defined above, and $R_t$ is hydrogen and $R_6$, $R_7$ and $R_8$ are as defined in relation to formula (I).

Of particular mention are the compounds wherein $R_1$ is $C_{1-6}$ alkyl, especially methyl, $R_2$, $R_3$, $R_4$ and $R_8$ are hydrogen, $R_6$ is 5-halo, especially 5-chloro, $R_7$ is 6-halo, especially 6-chloro, and X is a moiety $NR_sR_t$ wherein $R_t$ is hydrogen and $R_s$ is a moiety of formula (f) defined below or a moiety (H1) or (H2) as defined above, suitably wherein $R_s$ is a moiety of formula (H1) or (H2).

Of particular mention are the compounds wherein $R_1$ is $C_{1-6}$ alkyl, especially methyl, $R_2$, $R_3$, $R_4$ and $R_8$ are hydrogen, $R_6$ is 5-halo, especially 5-chloro, $R_7$ is 6-halo, especially 6-chloro, and X is a moiety $NR_sR_t$ wherein $R_t$ is hydrogen and Rs is a moiety (f), especially a moiety (f) wherein k is zero and $H_0$ is a moiety (a).

Of particular mention are the compounds wherein $R_1$ is $C_{1-6}$ alkyl, especially methyl, $R_2$, $R_3$, $R_4$ and $R_8$ are hydrogen, $R_6$ is 5-halo, especially 5-chloro, $R_7$ is 6-halo, especially 6-chloro, and X is a moiety $NR_sR_t$ wherein $R_t$ is hydrogen and Rs is a moiety (H1).

Of particular mention are the compounds wherein $R_1$ is $C_{1-6}$ alkyl, especially methyl, $R_2$, $R_3$, $R_4$ and $R_8$ are hydrogen, $R_6$ is 5-halo, especially 5-chloro, $R_7$ is 6-halo, especially 6-chloro, and X is a moiety $NR_sR_t$ wherein $R_t$ is hydrogen and Rs is a moiety (H2).

Particular examples of the invention are the compounds of example numbers 1, 31, 32 34, 35, 47, 48, 51, 55, 56, 59, 61, 62, 63, 68, 74 and 75.

Most particularly should be mentioned the compounds of example numbers 1, 55, 62, 68, 74 and 75.

The present invention does not encompass the examples per se of above mentioned co-pending International Application, application number PCT/EP96/0015 publication number WO 96/21644. Thus each of the examples of WO 96/21644 numbered 1 to 104 and each of the examples disclosed on page 50 are excluded from the present invention. Thus the invention excludes Examples 49, 51, 53, 59, 67, 69, 83, 84, 97 and 100 of WO 96/21644. Also, the invention excludes examples 33, 44, 48, 57, 65, 73, 91, 95, 98, 99, 101 and 10 of WO 96/21644. In addition the invention excludes examples 47, 56, 66 and 70 of WO 96/21644.

As used herein, the term "alkyl" includes straight or branched chain alkyl groups having from 1 to 12, suitably 1 to 6, preferably 1 to 4, carbon atoms, such as methyl, ethyl, n- and iso-propyl and n- iso-, tert-butyl and pentyl groups, and also includes such alkyl groups when forming part of other groups such as alkoxy or alkanoyl groups.

Suitable optional substituents for any alkyl group include hydroxy; alkoxy; a group of formula $NR_uR_v$ wherein $R_u$ and $R_v$ each independently represent hydrogen, optionally substituted alkyl, optionally substituted cycloalkyl, optionally substituted aryl, optionally substituted arylalkyl, optionally substituted heterocyclyl, optionally substituted heterocyclylalkyl, carboxy, carboxyalkyl, or alkoxycarbonyl, nitro, or $R_u$ and $R_v$ together with the nitrogen to which they are attached form an optionally substituted heterocyclic ring; carboxy; alkoxycarbonyl; alkoxycarbonylalkyl; alkylcarbonyloxy; alkylcarbonyl; mono- and di-alkylphosphonate; optionally substituted aryl; and optionally substituted heterocyclyl.

A preferred alkyl substituent is $NR_uR_v$, wherein $R_u$ and $R_v$ each independently represent hydrogen, optionally substituted aryl, optionally substituted arylalkyl, optionally substituted heterocyclyl, optionally substituted heterocyclylalkyl or $R_u$ and $R_v$ together with the nitrogen to which they are attached form an optionally substituted heterocyclic ring.

When $R_s$ or $R_t$ represents substituted alkyl, especially $C_{1-4}$ alkyl, particular substituent values are the moieties of formulae (a), (b), (c), (d) and (e):

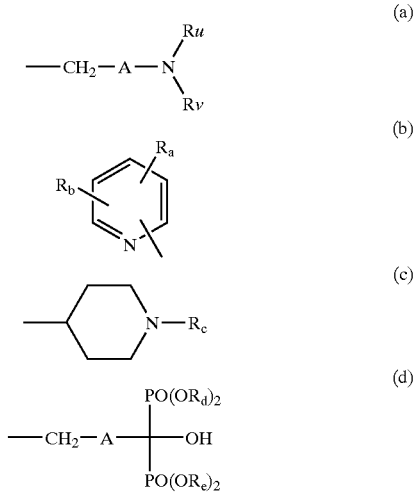

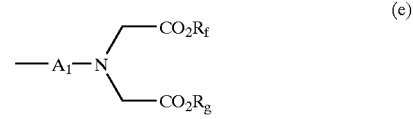

wherein A represents a bond or alkylene, suitably $C_{1-3}$ alkylene, $A_1$ is alkylene, suitably $C_{1-4}$ alkylene, and $R_a$, $R_b$, $R_c$, $R_d$, $R_e$, $R_f$ and $R_g$ each independently represent hydrogen, alkyl, optionally substituted aryl or an optionally substituted heterocyclic groupand $R_u$ and $R_v$ are as defined above.

One suitable alkyl substituent value is moiety (a).
One suitable alkyl substituent value is moiety (b).
One suitable alkyl substituent value is moiety (c).
One suitable alkyl substituent value is moiety (d).
One suitable alkyl substituent value is moiety (e).

In moiety (a), one preferred value for $NR_uR_v$ is a 1-piperazinyl group, preferably substituted in the 4 position with an acyl group, suitably a phenylcarbonyl group, or a heterocyclic group, such as a pyrimidyl group, or an optionally substituted phenyl group, such as a phenyl group with 1, 2 or 3 subsitutents selected from alkoxy, alkyl, trifluoromethyl, and halogen, for example chlorine and methoxy.

Thus one preferred value of $R_s$ or $R_t$ is a moiety of formula (f):

$$-(CH_2)_k-(H_0) \qquad (f)$$

wherein k is zero and $H_0$ is a moiety (a) or k is an integer 2 or 3 and $H_0$ is a moiety (b), (c), (d) and (e).

Preferably in moiety (f), k is zero and $H_0$ is a moiety (a).

As used herein, the term "alkenyl" includes straight or branched chain alkenyl groups having from 2 to 12, suitably 2 to 6 carbon and also includes such groups when forming part of other groups, an example is a butenyl group, such as a 2-butenyl group.

Suitable optional substituents for any alkenyl group includes the alkyl substituents mentioned above.

As used herein, the term "aryl" includes phenyl and naphthyl, especially phenyl.

Suitable optional substituents for any aryl group include up to 5 substituents, suitably up to 3 substituents, selected from alkyl, substituted alkyl, alkoxy, hydroxy, halogen, trifluoromethyl, acetyl, cyano, nitro, amino, mono- and di-alkylamino and alkylcarbonylamino.

Preferred optional substituents for any aryl group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy)hydroxymethyl, Suitable arylalkyl groups include aryl-$C_{1-3}$-alkyl groups such as phenylethyl and benzyl groups, especially benzyl.

Preferably, substituted aralkyl groups are substituted in the aryl moiety.

As used herein, the terms "heterocyclyl" or "heterocyclic" include saturated or unsaturated single or fused, ring heterocyclic groups, each ring having 4 to 11 ring atoms, especially 5 to 8, preferably 5, 6 or 7 which ring atoms include 1, 2 or 3 heteroatoms selected from O, S, or N.

As used herein 'fused ring heterocyclic group' includes polycyclic heterocyclic groups which share a single atom, such as a spiro ring system, one bond, as in an octahydroindolizinyl group, or more than one bond, as in an azabicyclo [3.2.1]oct-3-alpha-yl group.

Suitable optional substituents for any heterocyclyl or heterocyclic group include up to 5 substituents, suitably up to 3 substituents, selected from alkyl, substituted alkyl, alkoxy, hydroxy, halo, amino, mono- or di-alkyl amino, alkoxycarbonyl, hydroxyalkyl, alkoxyalkyl, hydroxyalkoxyalkyl, alkoxyalkyloxyalkyl, aryl, aryloxy and heterocyclyl.

Preferred optional substituents for any heterocyclyl or heterocyclic group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy) hydroxymethyl.

Further optional substituents for any heterocyclyl or heterocyclic group include up to 5, suitably up to 3, substituents selected from the list consisting of: isopropyl, cyano, oxo, arylcarbonyl, heterocyclyloxy, alkoxyalkoxy, alkoxycarbonylalkyloxy, carboxyalkyloxy, aminoalkyloxy, aminoalkylamino, aminoalkenylamino (especially aminomethyleneamino), alkanoylamino, alkoxyamino, aryl, acetamido, 2-(dimethylamino)ethylamino, 2-methoxyethoxy, 3-carboxyprop-2-oxy and 2-pyrazinyl.

Additional optional substituents for any hetrocyclyl or heterocyclic group include up to 5, suitably up to 3, substituents selected from the list consisting of: carbonylaminoalkyl, aminocarbonylalkyl and alkylcarbonylaminoalkyl.

For the avoidance of doubt a reference herein to "heterocyclic" includes a reference to "heterocyclyl".

As used herein, the term "halo" includes fluoro, chloro, bromo and iodo, suitably fluoro and chloro, favourably chloro.

Certain of the carbon atoms of the compounds of formula (I)—such as those compounds wherein $R_1$–$R_8$ contains chiral alkyl chains are chiral carbon atoms and may therefore provide stereoisomers of the compound of formula (I). The invention extends to all stereoisomeric forms of the compounds of formula (I) including enantiomers and mixtures thereof, including racemates. The different stereoisomeric forms may be separated or resolved one from the other by conventional methods or any given isomer may be obtained by conventional stereospecific or asymmetric syntheses.

The compounds of formula (I) also possess two double bonds and hence can exist in one or more geometric isomers. The invention extends to all such isomeric forms of the compounds of formula (I) including mixtures thereof. The different isomeric forms may be separated one from the other by conventional methods or any given isomer may be obtained by conventional synthetic methods. Suitable salts of the compounds of the formula (I) are pharmaceutically acceptable salts. A preferred isomer is the 2Z, 4E isomer.

Certain of the compounds herein can exist in various tautomeric forms, for example when hydroxy is a substituent on an aryl or heteroaryl ring; it is to be understood that the invention encompasses all such tautomeric forms.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

Suitable pharmaceutically acceptable salts of carboxy groups include metal salts, such as for example aluminium, alkali metal salts such as sodium or potassium and lithium, alkaline earth metal salts such as calcium or magnesium and ammonium or substituted ammonium salts, for example those with $C_{1-6}$ alkylamines such as triethylamine, hydroxy-$C_{1-6}$ alkylamines such as 2-hydroxyethylamine, bis(2-hydroxyethyl)-amine or tri-(2-hydroxyethyl)amine, cycloalkylamines such as dicyclohexylamine, or with procaine, 1,4-dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) or a salt thereof or a solvate thereof, may be prepared.

(a) for compounds of formula (I) wherein Ra represents hydrogen, alkyl or optionally substituted aryl and $R_b$ represents a moiety of the above defined formula (a), by reacting a compound of formula (II):

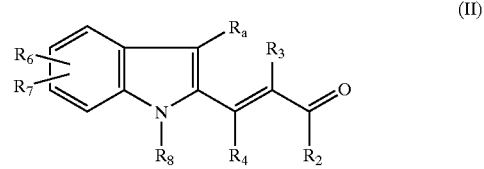

(II)

wherein $R_2$, $R_3$, $R_4$, $R_6$, $R_7$ and $R_8$ are as defined in relation to formula (I), with a reagent capable of converting a moiety of formula

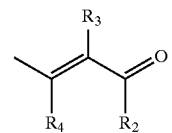

into a moiety of the above defined formula (a); or (b) for compounds of formula (I) where $R_a$ represents a moiety of the above defined formula (a) and $R_b$ represents hydrogen, alkyl or optionally substituted aryl, by treating a compound of formula (III):

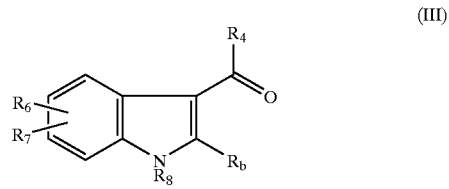

(III)

wherein $R_4$, $R_6$, $R_7$ and $R_8$ are as defined in relation to formula (I) with a compound of formula (IV):

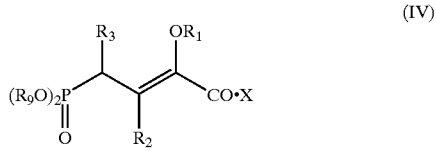

wherein $R_1$, $R_2$, $R_3$ and X are as defined in relation to the compounds of formula (I) and $R_9$ is a $C_{1-4}$ alkyl group; and thereafter, as necessary, carrying out one or more of the following reactions:
(i) converting one compound of formula (I) into another compound of formula (I);
(ii) removing any protecting group;
(iii) preparing a salt or a solvate of the compound so formed.

In reaction (a) above, a suitable reagent capable of converting a moiety of the above defined formula

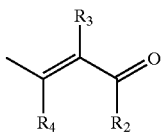

into a moiety of the above defined formula (a), includes conventional reagents used to convert C=O bonds into carbon carbon double bonds, such as Wittig or Horner-Emmons reagents, for example those of formula (V):

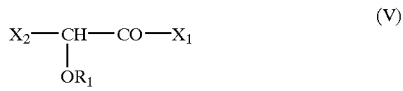

wherein $R_1$ is as defined in relation to the compounds of formula (I), $X_1$ represents X as defined in relation to formula (I) or a group convertible thereto and $X_2$ represents a moiety $(R_9O)_2P(O)$— wherein $R_9$ is as defined above or a group $Ph_3P$—.

The reaction between the compounds of formula (II) and the reagent capable of converting the group of formula

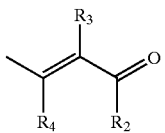

into the moiety of formula (a), may be carried out under the appropriate conventional conditions, depending upon the particular reagent chosen, for example:

When the reagent is a compound of formula (V) wherein $X_2$ is a moiety $(R_9O)_2P(O)$—, then the reaction is carried out under conventional Horner-Emmons conditions, using any suitable, aprotic solvent for example an aromatic hydrocarbon such as benzene, toluene or xylene, DMF, DMSO, chloroform, dioxane, dichloromethane, preferably, THF, acetonitrile, N-methylpyrrolidone, and the like or mixtures thereof, preferably an anhydrous solvent, at a temperature providing a suitable rate of formation of the required product, conveniently at ambient temperature or at an elevated temperature, such as a temperature in the range of from 30° C. to 120° C.; preferably the reaction is conducted in the presence of a base.

Suitable bases for use in the last above mentioned reaction include organic bases, such as butyl lithium, lithium diisopropylamide (LDA), N,N-diisopropylethylamine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as sodium hydride; preferably sodium hydride, and generally the reaction is carried out in an inert atmosphere such as nitrogen.

When the reagent is a compound of formula (V) wherein $X_2$ is a moiety $Ph_3P$—, then the reaction is carried out under conventional Wittig conditions. Usually, the reaction is carried out in the presence of a base, in any suitable aprotic solvent. Suitable bases are organic bases such as triethylamine, trimethylamine, N,N-diisopropylethylamine (DIPEA), pyridine, N,N-dimethylaniline, N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO) and inorganic bases such as sodium hydride, caesium carbonate, potassium carbonate, preferably sodium hydride. Suitable solvents are conventional solvents for use in this type of reaction, such as aromatic hydrocarbons such as benzene, toluene or xylene or the like; DMF, DMSO, chloroform, dioxane, dichloromethane, THF, ethyl acetate, acetonitrile, N-methylpyrrolidone or mixtures thereof, preferably dichloromethane. This reaction is carried out at any temperature providing a suitable rate of formation of the required product, conveniently at ambient temperature or at an elevated temperature, such as a temperature in the range of from −20° C. to 140° C., preferably in the range of from about room temperature to the reflux temperature of the solvent.

The reaction between the compounds of formula (III) and the Horner Emmons reagent of formula (IV) may be carried out under conventional Horner Emmons conditions such as those described above.

A compound of formula (II) may be prepared according to the reaction sequences shown in Schemes (Ia-c) below Scheme (Ia)

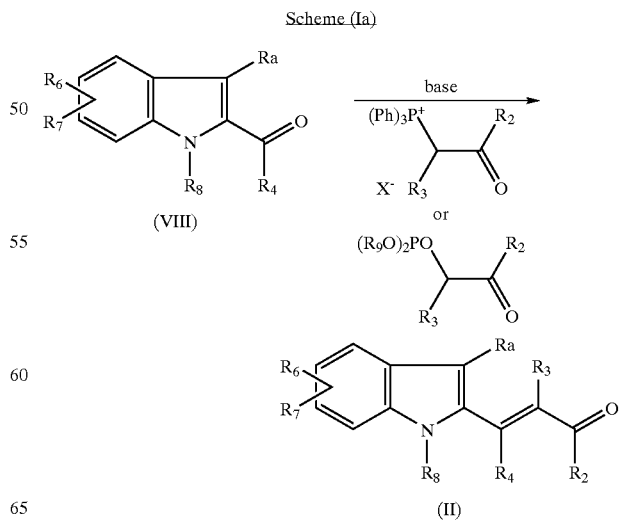

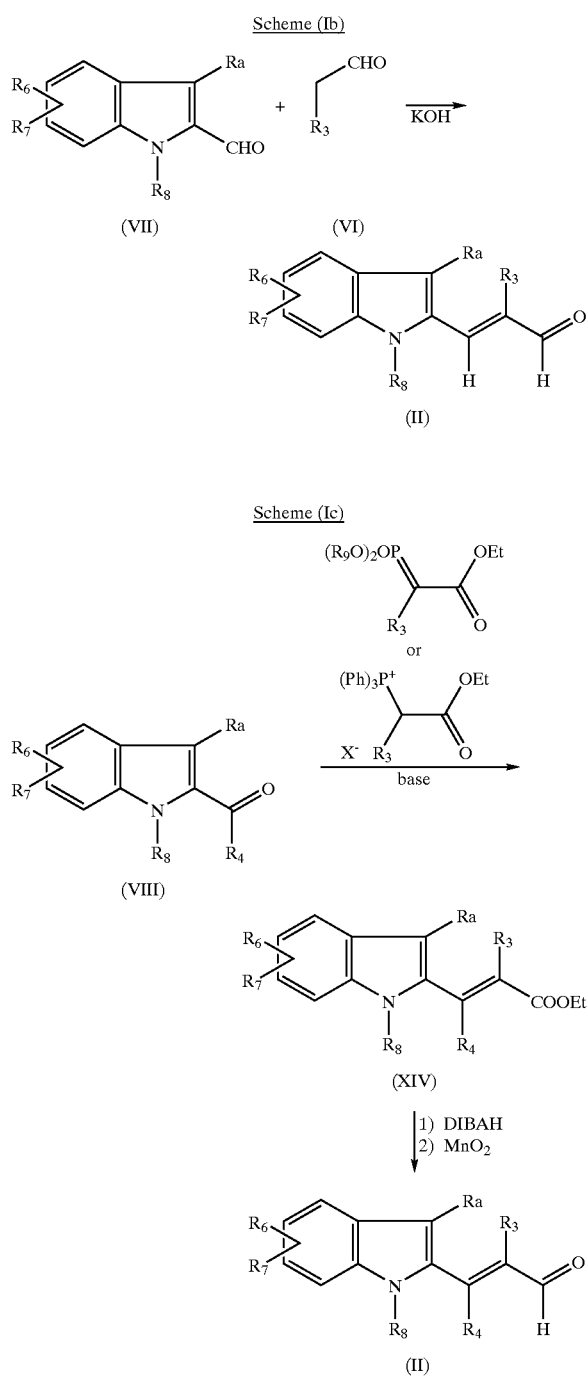

wherein, subject to any qualification mentioned below, $R_a$, $R_2$, $R_3$, $R_4$, $R_6$, $R_7$ and $R_8$ are as defined in relation to the compounds of formula (I).

Compounds of formula (II) may be prepared using either Wittig or Horner-Emmons reactions of keto derivatives of formula (VIII) with the appropriate phosphonium salt or phosphonate using the reaction conditions which are known in the art and described, for example in "The Wittig Reaction", R. Adams Ed., Vol. 14, p. 270 (1965) or in Angew. Chem. Int. Ed. Engl., 4, 645 (1965).

When $R_2$ is other than —H, e.g. alkyl, a compound of formula (II) is obtained directly from a compound of formula (VIII) by Wittig or Horner-Emmons reaction with the appropriate phosphonium salts or phosphonates according to Scheme (Ia).

When a compound of formula (VIII) is reacted with the above mentioned phosphonates using the Horner-Emmons reaction, the experimental conditions used are conventional conditions such as those reported, in Tetrahedron Lett. 1981, 461; Can. J. Chem., 55, 562 (1977); J. Am. Chem. Soc., 102, 1390 (1980); J. Org. Chem., 44, 719 (1979); Synthesis, 1982, 391; and Tetrahedron Lett. 1982, 2183.

The reaction of compounds of formula (VIII) with the above mentioned phosphonium salts are carried out in the presence of a base in any suitable solvent. Suitable bases include organic bases, such as triethylamine, trimethylamine, N,N-diisopropylethylamine (DIPEA), pyridine, N,N-dimethylaniline, N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO) and inorganic bases, such as sodium hydride, caesium carbonate, potassium carbonate. Suitable solvents include conventionally used solvents, for example aromatic hydrocarbons such as benzene, toluene or xylene or the like; DMF, DMSO, chloroform, dioxane, dichloromethane, THF, ethyl acetate, acetonitrile, N-methylpyrrolidone and the like or mixtures thereof. Preferably, the reaction is carried out at a reaction temperature of in the range of about −20° C. to 140° C., preferably about room temperature to the reflux temperature of the solvent.

The reaction of compounds of formula (VIII) with phosphonates are carried out under conventional Horner-Emmons conditions, using any suitable, aprotic solvent for example an aromatic hydrocarbon such as benzene, toluene or xylene, DMF, DMSO, chloroform, dioxane, dichloromethane, preferably, THF, acetonitrile, N-methylpyrrolidone, and the like or mixtures thereof, preferably an anhydrous solvent, at a temperature providing a suitable rate of formation of the required product, conveniently at ambient temperature or at an elevated temperature, such as a temperature in the range of from 30° C. to 120° C.; preferably the reaction is conducted in the presence of a base.

Suitable bases for use in the last above mentioned reaction include organic bases, such as butyl lithium, lithium diisopropylamide (LDA), N,N-diisopropylethylamine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as sodium hydride; preferably sodium hydride, and generally the reaction is carried out in an inert atmosphere such as nitrogen.

When $R_2$=H, aldehyde (VII) is reacted with aliphatic aldehydes of formula (VI) in presence of bases such as sodium or potassium hydroxide affording compound (II) as in Scheme (Ib), using the appropriate conventional procedure In a further aspect, when $R_2$=H, a compound of formula (VIII) is reacted with a substituted carbethoxymethylphosphonium salt or carbethoxymethylphosphonate (Scheme (Ic)), the carboxylic ester obtained (XIV) is then converted into the corresponding alcohol with a reducing agent, suitably a complex metal reducing agent such as lithium aluminium hydride (LiAlH$_4$), diisobutyl aluminium hydride (DIBAH) or lithium borohydride (LiBH$_4$), in any suitable aprotic solvent for example methylene dichloride, chloroform, dioxane, diethyl ether or THF, at any temperature providing a suitable rate of formation of the required product, such as a temperature in the range of from −30° C. to 60° C., for example at room temperature. Then, the intermediate alcohol is oxidised to aldehyde (II) with an oxidising agent such as manganese dioxide, periodinane (Dess-Martin reagent), pyridinium chlorochromate (PCC) or pyridinium dichromate (PDC) or a combination of oxalyl chloride and DMSO (Swern reaction), preferably manganese dioxide in methylene dichloride.

A compound of formula (IV) may be prepared according to the reaction sequence shown in Scheme (II) below.

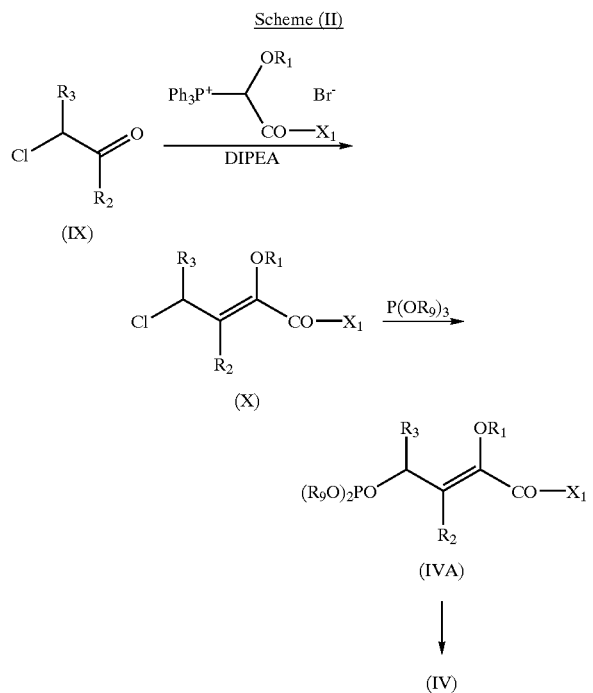

wherein, subject to any qualification mentioned below, $R_1$, $R_2$ and $R_3$ are as defined in relation to formula (I), $R_9$ is as defined in relation to formula (IV) and $X_1$ is as defined in relation to formula (V).

Compounds of formula (X) are prepared by reaction of, preferably anhydrous, chloroaldehydes or chloroketones of formula (IX) with suitable phosphonium compounds using the appropriate conventional procedure as described above for the Wittig reaction; conversion of intermediate compound (X) into the desired compound (IV) may be effected by reaction with a suitable trialkylphosphite $(R_9O)_3P$ wherein $R_9$ is as defined above, and the reaction is performed in any conventionally used solvent, preferably the trialkyl phosphite, and at a suitable reaction temperature, preferably at the boiling point of the solvent. For example from Scheme (II): the chloroacetaldehyde (IX) was treated with methyl 2-methoxy-2-(triphenylphosphonium)acetate bromide in the presence of DIPEA in chloroform and the intermediate (X) so obtained was converted into compound (IV) by refluxing in trimethyl phosphite.

The compounds of formula (V) can be prepared according to the reaction sequence shown in Scheme (III) below:

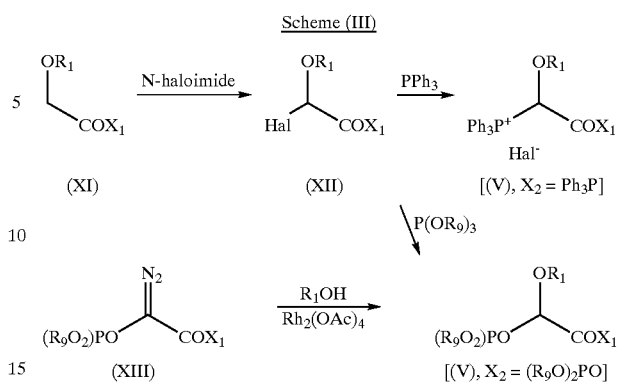

wherein, subject to any qualification mentioned below, $R_1$ and $R_9$ are as defined in relation to formula (I) and $X_1$ is as defined in relation to formula (V).

The starting material is an α-alkoxycarboxylic ester of formula (XI) which is commercially available or which is prepared according to the methods known in the art, for example those reported in Rodd's Chemistry of Organic Compounds, Vol ID, p. 96 (1965), S. Coffey Ed., Elseviers. The compound of formula (XI) is reacted with an N-haloimide, for example N-bromosuccinimide in the presence of a radical producing agent such as azobisisobutyronitrile or benzoyl peroxide in a suitable solvent such as carbon tetrachloride, benzene, for example carbon tetrachloride and at a reaction temperature in the range of from −30° C. and 80° C., for example at room temperature; examples of such a reaction may be found in the literature, for example J. Org. Chem., 41, 2846 (1976). The halocompound obtained, of formula (XII), is then reacted either with triphenylphosphine or with a trialkyl phosphite $P(OR_9)_3$ to give the required compound of formula (V) as shown in scheme (III).

When the compound of formula (XII) is reacted with triphenylphosphine, the reaction is performed in any conventionally used solvent, for example diethyl ether, dioxane, tetrahydrofuran, benzene, xylene or, preferably, toluene at a suitable reaction temperature in the range of from −30° C. to 80° C., for example at room temperature (examples of this conversion are reported in the literature, for example in Chem. Ber., 97, 1713 (1964)).

When the compound of formula (XII) is reacted with trialkyl phosphite $P(OR_9)_3$, the reaction is performed in any conventionally used solvent, preferably the trialkyl phosphite, and at a suitable reaction temperature, preferably at the boiling point of the solvent (examples of this conversion are reported in the literature, for example in Liebigs Ann. Chem., 699, 53 (1966)).

Alternatively, a compound of formula (V) in which $R_2$ is $(R_9O)_2PO$ may be prepared using the procedure depicted in Scheme (III), by reacting a diazophosphonoacetates of formula (XIII) with an alcohol or phenol of formula $R_1OH$, wherein $R_1$ is as defined in relation to formula (I), in the presence of rhodium (II) acetate as described in the literature, for example in Tetrahedron, 50, 3177 (1994) or in Tetrahedron, 48, 3991 (1992).

The compounds of formula (III), (VII) and (VIII), are known compounds or they are prepared using methods analogous to those used to prepare known compounds, such as those described in J. Org. Chem., 47, 757 (1982); Heterocycles, 22, 1211 (1984); Tetrahedron, 44, 443 (1988), Liebigs Ann. Chem., 1986, 438; Chem. Pharm. Bull., 20, 76, 1972.

The compounds of formula (VI), (IX) and (XI) are known compounds or they are prepared using methods analogous to those used to prepare known compounds, such as those described in J. March, *Advanced Organic Chemistry*, 3rd Edition (1985), Wiley Interscience.

Suitable conversions of one compound of formula (I) into another compound of formula (I) includes converting a compound of formula (I) wherein X represents a hydroxy group or an alkoxy group into a compound of formula (I) wherein X represents a different alkoxy group or a moiety of the above defined formula $NR_sR_t$. Such conversions are shown below in Scheme (IV):

(i) when X is alkoxy, by basic hydrolysis, using for example potassium hydroxide, to provide a compound of formula (I) wherein X is hydroxy, and thereafter (a) for preparing compounds wherein X represents a moiety of the above defined formula $NR_sR_t$, treating with a compound of formula $HNR_{s'}R_{t'}$ wherein $R_{s'}$ and $R_{t'}$ are as defined above or (b) for preparing compounds of formula (I) wherein X represents alkoxy, by treating with a compound of formula R'OH wherein R' is the required alkyl group; and thereafter optionally deprotecting; or (ii) when X is hydroxy, by using analogous procedures to those mentioned above in (i).

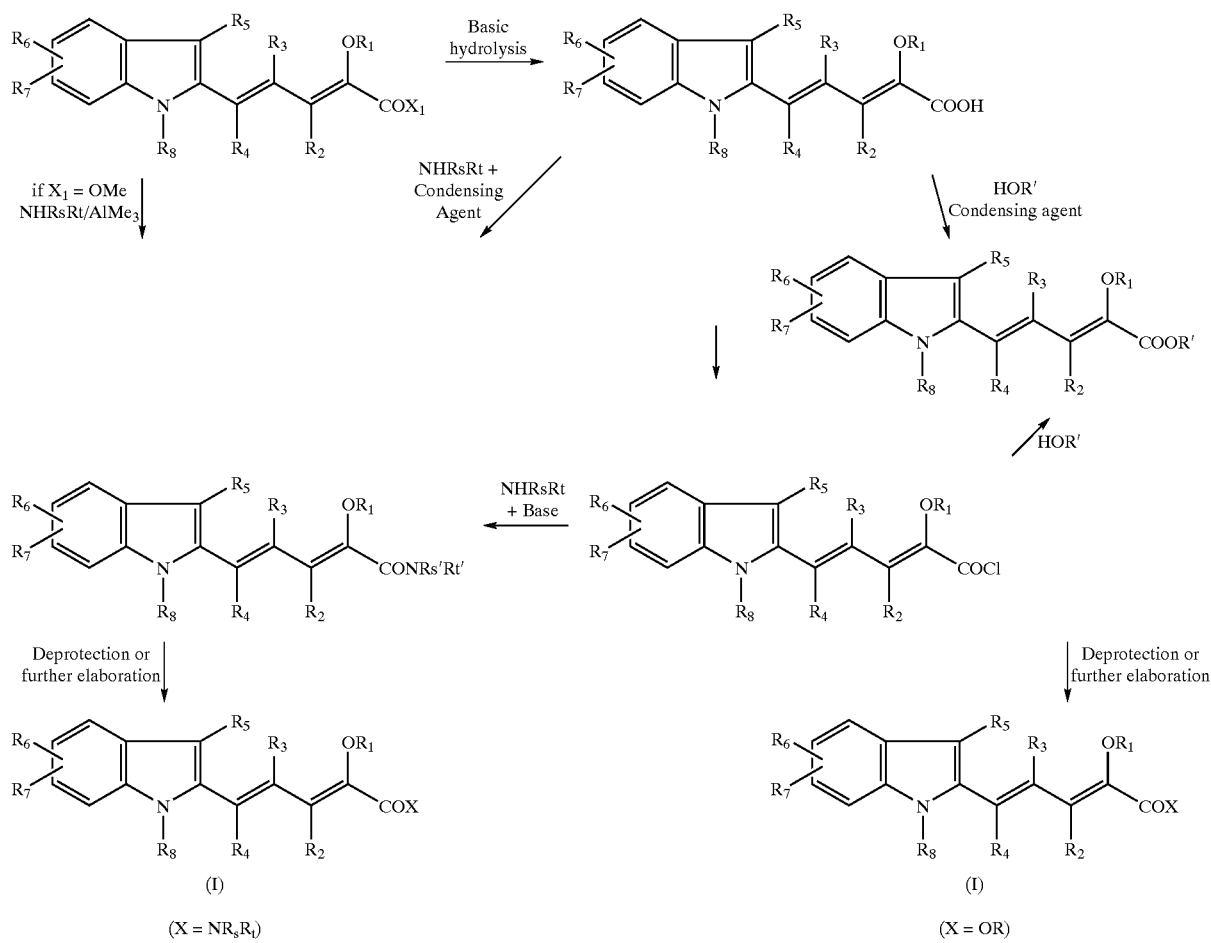

Scheme (IV)

wherein, subject to any qualification mentioned below, $R_2$, $R_3$, $R_4$, $R_5$, $R_6$, $R_7$, $R_8$ and X are as defined in relation to the compounds of formula (I), $R_{s'}$ is $R_s$ or a protected form thereof, $R_{t'}$ is $R_t$ or a protected form thereof and R' is X when X is an alkoxy group.

The conversion of one compound of formula (I) into another compound of formula (I) may be carried out using the appropriate conventional procedure; for example, the above mentioned conversion of a compound wherein X represents a hydroxy group or an alkoxy group into a compound wherein X represents a moiety of the above defined formula $NR_sR_t$ or another alkoxy group may be carried out as follows:

Preferably the reaction with the compounds of formula $HNR_{s'}R_{t'}$ or with compounds of formula R'OH takes place after activation of the carboxylic group.

A carboxyl group may be activated in conventional manner, for example, by conversion into an acid anhydride, acid halide, acid azide or an activated ester such as cyanomethyl ester, thiophenyl ester, p-nitrophenyl ester, p-nityrothiophenyl ester, 2,4,6-trichlorophenyl ester, pentachlorophenyl ester, pentafluorophenyl ester, N-hydroxyphthalimido ester, 8-hydroxypiperidine ester, N-hydroxysuccinimide ester, N-hydroxybenzotriazole ester, or the carboxyl group may be activated using a carbodiimide such as N,N'-dicyclohexylcarbodiimide (DCC) or 1-ethyl-3-[3-(dimethylamino)propyl]-carbodiimide hydrochloride (WSC), either in the presence or the absence of hydroxybenzotriazole (HOBt) or 1-hydroxy-7-azabenzotriazole (HOAt); or it may be activated using N,N'-carbonyldiimidazole, Woodward-K reagent, Castro's reagent or an isoxazolium salt.

Condensation of an activated carboxyl group with an amino group or with an alcoholic group may be carried out in the presence of a base, in any suitable solvent. Suitable bases include organic bases, such as triethylamine, trimethylamine, N,N-diisopropylethylamine (DIPEA), pyridine, N,N-dimethylaniline, 4-dimethylaminopyridine (DMAP), N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as potassium carbonate. Suitable solvents include conventionally used solvents, for example DMF, dimethyl sulfoxide (DMSO), pyridine, chloroform, dioxane, dichloromethane, THF, ethyl acetate, acetonitrile, N-methylpyrrolidone and hexamethylphosphoric triamide and mixtures thereof. The reaction temperature may be within the usual temperature range employed in this type of condensation reaction, and generally in the range of about −40° C. to about 60° C., preferably from about −20° C. to about 40° C.

When the reaction is carried out in the presence of a suitable condensing agent, for example a carbodiimide, N,N'-carbonyldiimidazole, Woodward-K reagent, Castro's reagent or the like, the condensing agent is preferably employed in an amount from equimolar to about 5 times the molar quantity of the starting material and the reaction is performed in a suitable solvent for example a halogenated hydrocarbon such as dichloromethane, chloroform, carbon tetrachloride, tetrachloroethane or the like; an ether such as dioxane, THF, dimethoxyethane or the like, a ketone such as acetone, methyl ethyl ketone or the like; acetonitrile, ethyl acetate, DMF, dimethylacetamide, DMSO or the like. Preferably the condensation is carried out in an anhydrous solvent, and at a reaction temperature in the range of from about −10° C. to 60° C., preferably about 0° C. to room temperature.

Alternatively, conversion of one compound of formula (I) in which X is O-alkyl into another compound of formula (I) in which X is $NR_sR_t$, may be effected by treating the said compound of formula (I) directly with a compound of formula $HNR_sR_t$, in the presence of a trialkylaluminium reagent such as trimethylaluminium or triethylaluminium, according to known procedures, such as those disclosed in Tetrahedron Lett., 48, 4171 (1977); and, if necessary, deprotecting or converting the compound of formula (I) in which X is $NR_sR_t$, into a compound of formula (I) in which X is $NR_sR_t$.

The trialkylaluminium reagent is generally employed in the above mentioned reactions in an amount of from equimolar to about 5 times the molar quantity of the starting material, preferably 2–3 times the molar quantity of the starting material and the reaction is performed in a suitable solvent for example a halogenated hydrocarbon such as dichloromethane, chloroform, carbon tetrachloride, tetrachloroethane or the like; an ether such as dioxane, THF, dimethoxyethane or the like. Preferably the condensation is carried out in an anhydrous solvent, and at a reaction temperature of about, generally −20° C. to 120° C., preferably about 0° C. to the reflux temperature of the solvent.

Amines of general formula $HNR_sR_t$ may be prepared using the methods known in the art for the preparation of amines, for example as taught in Houben-Weil, Methoden der Organischen Chemie, Vol. XI/1 (1957) and Vol. E16d/2 (1992), Georg Thieme Verlag, Stuttgart.

In particular, amines of the general formula $HNR_sR_t$ wherein one of $R_s$ and $R_t$ represents hydrogen and the other represents a moiety (a), (b), (c), (d) (e) as defined above or a particular example thereof, are prepared according to the methods summarised in Scheme (V) below:

Scheme (V)

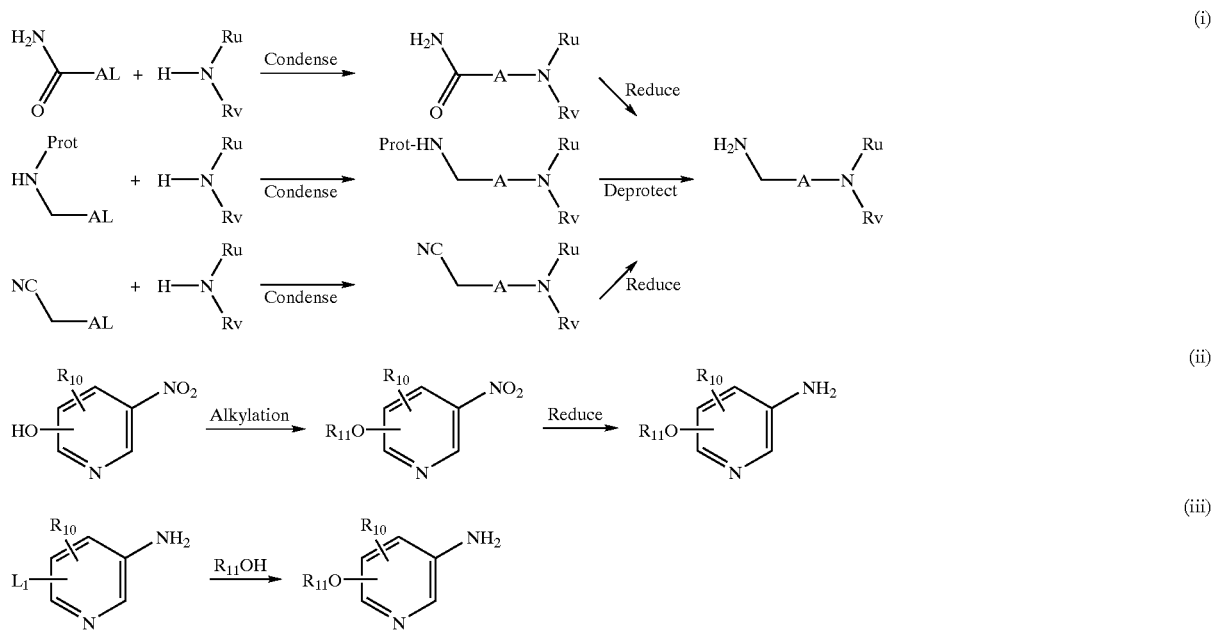

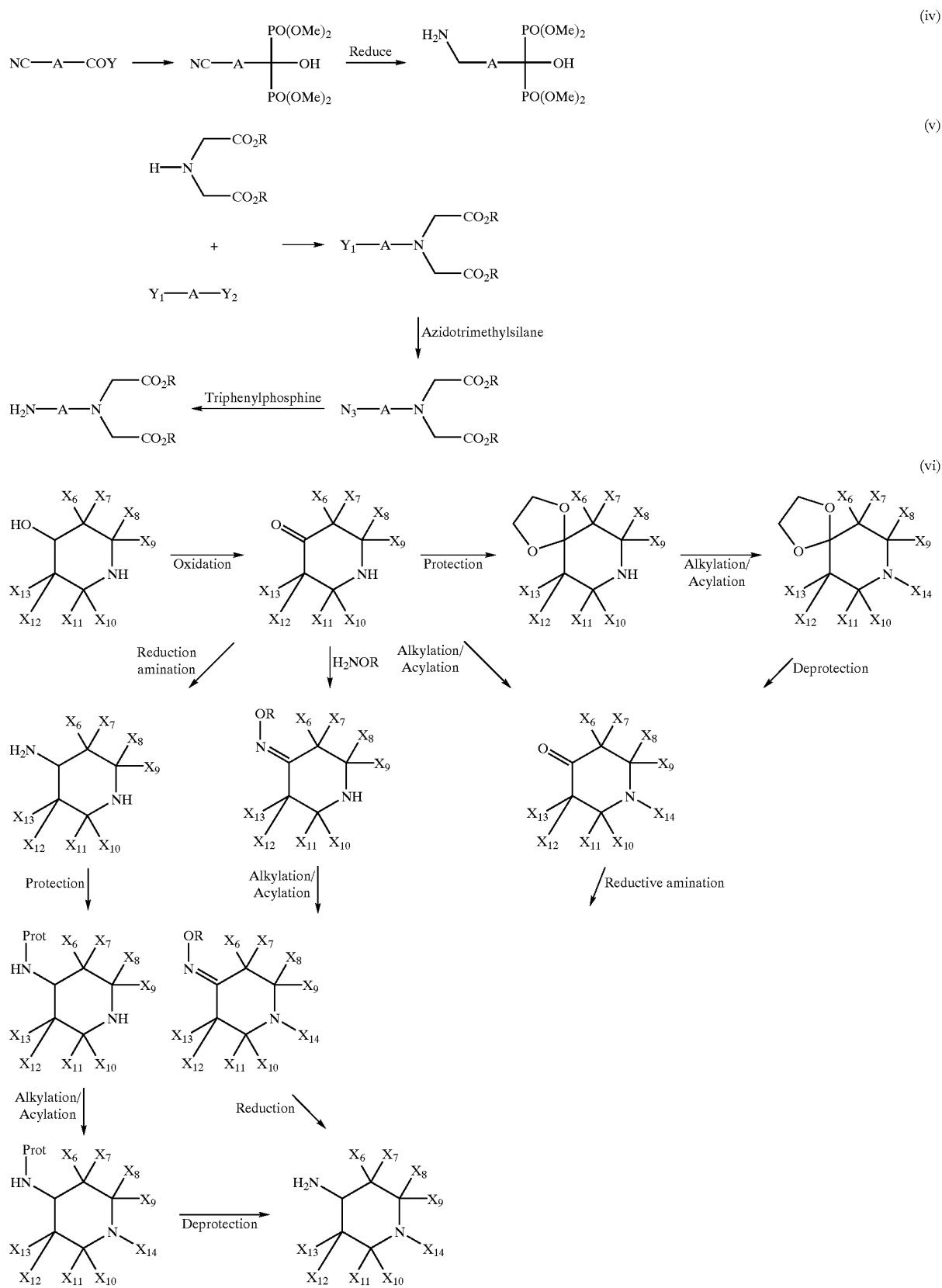

(vii)

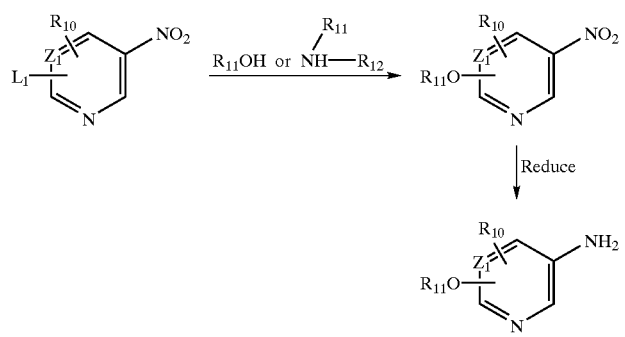 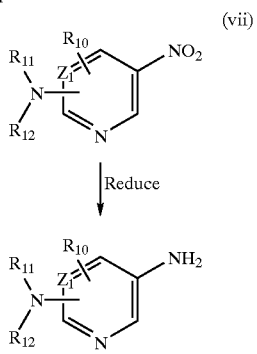

wherein R is an alkyl or aryl group, $R_u$ and $R_v$ are as defined above, $X_6$ to $X_{14}$ are as defined for (H2), A is a bond or an alkylene chain, $R_{10}$ is hydrogen (in (ii) and (vii)) or halogen (in (iii)) and $R_{11}$ is an alkyl group, $R_{12}$ is alkyl or aryl, L and $L_1$ are leaving groups, for example halogen or mesylate, Y is halogen, $Y_1$ is a leaving group, for example a halogen and and $Y_1$ and $Y_2$ are leaving groups such as halogens, for example $Y_1$ is chloride and $Y_2$ is bromine, $Z_1$ is N or $CY_3$ wherein $Y_3$ is selected from hydrogen, alkyl, alkoxy, alkylcarbonyl, aryl, aryloxy or arylcarbonyl.

The reactions of condensation in (i) are performed under conventional reaction conditions as described in J. March, *Advanced Organic Chemistry*, 3rd Edition, 1985, Wiley Interscience The reduction of the amide function in (i) is suitably carried out using known methods, for example by using mixed hydride reducing agents, such as lithium aluminium hydride and methods described in *Org Synth Coll* Vol 4 564.

Protection of the primary amino group in (i) can entail the use of classical carbamate protecting agents such as t-butoxycarbonyl (Boc), benzyloxycarbonyl (Cbz) or fluorenylmethoxycarbonyl (Fmoc), or of the phthalimido protecting group. The synthesis and the removal of such protective groups is described in, for example, in *Protective Groups in Organic Synthesis*, T. W Greene Ed., Wiley, New York, 1981

The reduction of the nitrile in (i) is suitably carried out using known methods, for example following the procedure described in *J. Med. Chem.*, 39, 1514, (1996).

The reduction of the nitropyridine in (ii) is suitably carried out using the method described in *J. Org. Chem.* 58, 4742 (1993).

The alkylation of the hydroxy-nitropyridine in (ii) may be effected by using the method described in *J. Org. Chem* 55, 2964 (1990).

The displacement reaction in (iii) and (vii) is suitably carried out using the method described in *Helvetica Chemica Acta* 47 (2),45 (1964)

The reduction of the nitrile in (v) is suitably carried by catalytic hydrogenation over platinium oxide.

The reduction of nitro group in (vii) is suitably carried out using the method described in *J. Org. Chem.* 58, 4742 (1993).

The reaction of acid halide NC-A-COY to provide the dialkylphosphonate in (iv) is effected by following the procedure described in *J Org Chem* 36, 3843 (1971).

The reaction of the azide with triphenylphosphine in (v) is carried out in wet tetrahydrofuran as described in *Bull Soc Chim Fr* 1985, 815.

The azides in (v) are prepared as shown using azidotrimethylsilane, following the procedure described in *Synthesis* 1995, 376.

The reaction of compound $Y_1$-A-$Y_2$ and the amine derivative in (v) proceeds under conventional displacement reaction conditions.

The reactions in (vi) can be performed using known, conventional methods, as described in J. March, *Advanced Organic Chemistry*, 3rd Edition, 1985, Wiley Interscience. For example, oxidation can be performed using oxidising agents such as chromic acid (Jones reagent); reductive amination of the ketone in can be performed with benzylamine to give an imine intermediate which is then reduced using known methods and reducing agents such as sodium borohydride or lithium aluminium hydride. Debenzylation can then be performed again using conventional methods, for example with hydrogen in the presence of a catalyst such as palladium on charcoal. Protection of ketone as the ethylene ketal can be performed with ethylene glycol under acidic catalysis; acylations or alkylations can be performed by treating the suitable piperidine derivatives with acyl or alkyl halides in the presence of an inorganic or organic base; deprotection of the dioxolane to the ketone can be effected by acidic treatment in aqueous or alcoholic solvents. Protection on the primary amino group in 4 aminopiperidines can entail the use of classical carbamate protecting agents such as t-butoxycarbonyl (Boc), benzyloxycarbonyl (Cbz) or fluorenylmethoxycarbonyl (Fmoc), or of the phthalimido protecting group: the synthesis and the removal of such protective groups is described in, for example, in *Protective Groups in Organic Synthesis*, T. W Greene Ed., Wiley, New York, 1981. 4-Oxopiperidines can be converted into the corresponding oximes by treatment with hydroxyl- or alkoxyl-amine in a suitable solvent; reduction of the oxime to amine can be performed using conventional reducing agents such as lithium aluminium hydride or sodium cyanoborohydryde.

The starting materials in the above reactions (i), (ii), (iii), (iv), (v), (vi) and (vii) are known, commercially available compounds.

A compound of formula (I) or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers and diastereoisomers by conventional means, for example by the use of an optically active acid as a resolving agent. Suitable optically active acids which may be used as resolving agents are described in "*Topics in Stereochemistry*", Vol. 6, Wiley Interscience, 1971, Allinger, N. L. and Eliel, W. L. Eds.

Alternatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group or atom, may be carried out at any appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropriate silylating agent such as di-tert-butylsilylbis (trifluoromethanesulfonate): the silyl group may then be removed using conventional procedures such as treatment with hydrogen fluoride, preferably in the form of a pyridine complex and optionally in the presence of alumina, or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in ethyl acetate or trifluoroacetic acid in methylene dichloride. An amino group may be protected as a benzyl derivative, prepared from the appropriate amine and a benzyl halide under basic conditions, the benzyl group being removed by catalytic hydrogenolysis, using for example a palladium on carbon catalyst.

Indole NH groups and the like may be protected using any conventional group, for example benzenesulphonyl, methylsulphonyl, tosyl, formyl, acetyl (all of them removable by treatment with alkaline reagents), benzyl (removable either with sodium in liquid ammonia or with $AlCl_3$ in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl) ethoxymethyl (SEM) (removable by treatment with tetrabutylammonium fluoride in the presence of ethylendiamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The salts, esters, amides and solvates of the compounds mentioned herein may as required be produced by methods conventional in the art: for example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_sR_t$ may be prepared by treating the relevant carboxylic acid with an amine of formula $HN R_sR_t$ wherein $R_s$ and $R_t$ are as defined above. Alternatively, a $C_{1-6}$ alkyl ester such as a methyl ester of the acid may be treated with an amine of the above defined formula $HNR_sR_t$ to provide the required amide.

As mentioned above the compounds of the invention are indicated as having useful therapeutic properties:

The present invention therefore provides a method for the treatment and/or prophylaxis of diseases associated with over activity of osteoclasts in mammals which method comprises the administration of an effective non-toxic amount of a selective inhibitor of mammalian osteoclasts.

A suitable selective inhibitor of a mammalian osteoclast is a selective inhibitor of the vacuolar ATPase located on the ruffled border of mammalian osteoclasts.

One particular selective inhibitor of mammalian vacuolar ATPase is a compound of formula (I), or a pharmaceutically acceptable salt thereof, or a pharmaceutically acceptable solvate thereof.

Thus, the present invention further provides a method for the treatment of osteoporosis and related osteopenic diseases in a human or non-human mammal, which comprises administering an effective, non-toxic, amount of a compound of formula (I) or a pharmaceutically acceptable solvate thereof, to a human or non-human mammal in need thereof.

In a further aspect, the present invention provides an inhibitor of a mammalian, especially human, osteoclasts, for example a compound of formula (I) or a pharmaceutically acceptable salt thereof, or a pharmaceutically acceptable solvate thereof, for use as an active therapeutic substance.

The preferred mammal is human. Mammalian osteoclasts are preferably human osteoclasts.

In particular the present invention provides a compound of formula (I) or a pharmaceutically acceptable salt thereof and/or a pharmaceutically acceptable solvate thereof, for use in the treatment of and/or prophylaxis of osteoporosis and related osteopenic diseases.

Of particular interest is the osteoporosis associated with the peri and post menopausal conditions. Also encompassed are the treatment and prophylaxis of Paget's disease, hypercalcemia associated with bone neoplasms and all the types of osteoporotic diseases as classified below according to their etiology:

Primary osteoporosis
   Involutional
      Type I or postmenopausal
      Type II or senile
   Juvenile
   Idiopathic in young adults
Secondary osteoporosis
   Endocrine abnormality
      Hyperthyroidism
      Hypogonadism
      Ovarian agenesis or Turner's syndrome
      Hyperadrenocorticism or Cushing's syndrome
      Hyperparathyroidism
   Bone marrow abnormalities
      Multiple myeloma and related disorders
      Systemic mastocytosis Disseminated carcinoma
Gaucher's disease
Connective tissue abnormalities
Osteogenesis imperfecta
Homocystinuria
Ehlers-Danlos syndrome
Marfan's syndrome
Menke's syndrome
Miscellaneous causes
Immobilisation or weightlessness
Sudeck's atrophy
Chronic obstructive pulmonary disease
Chronic alcoholism
Chronic heparin administration
Chronic ingestion of anticonvulsant drugs In addition the invention encompasses the treatment of tumours, especially those related to renal cancer, melanoma, colon cancer, lung cancer and leukemia, viral conditions (for example those involving Semliki Forest virus, Vesicular Stomatitis virus, Newcastle Disease virus, Influenza A and B viruses, HIV virus), ulcers (for example chronic gastritis and peptic ulcer induced by Helicobacter pylori), for use as immunosupressant agents in autoimmune diseases and transplantation, antilipidemic agents for the treatment and/or prevention of hypercholesterolemic and atherosclerotic diseases and to be useful for the treatment of AIDS and Alzheimer's disease. These compounds are also considered useful in treating angiogenic diseases, i.e. those pathological conditions which are dependent on angiogenesis, such as rheumatoid arthritis, diabetic retinopathy, psoriasis and solid tumours A selective inhibitor of the pharmacological activity of human osteoclast cells such as a compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a selective inhibitor of the pharmacological activity of human osteoclast cells, in particular the bone resorption activity of human osteoclast cells associated with abnormal loss of bone mass, and a pharmaceutically acceptable carrier thereof.

A particular inhibitor of human osteoclast cells is a selective inhibitor of human osteoclast vacuolar ATPase such as a compound of formula (I), or a pharmaceutically acceptable salt thereof, or a pharmaceutically acceptable solvate thereof, and a pharmaceutically acceptable carrier thereof.

Active compounds or a pharmaceutically acceptable salt thereof and/or a pharmaceutically acceptable solvate thereof is normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated and the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily dose is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

At the above described dosage range, no toxicological effects are indicated for the compounds of the invention.

The present invention also provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by Helicobacter pylori), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours, in a human or non-human mammal, which comprises administering an effective, non-toxic, amount of a compound of formula (I) or a pharmaceutically acceptable solvate thereof, to a human or non-human mammal in need thereof.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles,- reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as 'Dermatological Formulations'—B. W. Barry (Drugs and the Pharmaceutical Sciences—Dekker) or Harrys Cosmeticology (Leonard Hill Books).

The present invention also provides the use of a selective inhibitor of the biological activity of human osteoclast cells, in particular the bone resorption activity of human osteoclast cells associated with abnormal loss of bone mass, compound of formula (I), or a pharmaceutically acceptable salt thereof, or a pharmaceutically acceptable solvate thereof, for the manufacture of a medicament for the treatment and/or prophylaxis of diseases associated with over activity of osteoclasts in mammals, such as the treatment and/or prophylaxis of osteoporosis and related osteopenic diseases.

The present invention also provides the use of a selective inhibitor of the biological activity of human osteoclast cells, in particular the bone resorption activity of human osteoclast cells associated with abnormal loss of bone mass, for the manufacture of a medicament for the treatment of tumours, especially those related to renal cancer, melanoma, colon cancer, lung cancer and leukemia, viral conditions (for example those involving Semliki Forest, *Vesicular Stomatitis, Newcastle Disease*, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours.

In one preferred aspect the inventions herein comprising compositions, treatment methods and pharmaceutical uses of a selective inhibitor of the biological activity of mammalian, including human, osteoclast cells exclude the compositions, treatment methods and pharmaceutical uses of the compounds of formula (I) of WO96/21644 and in another aspect the specific examples of WO96/21644.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

Preparation 1

Ethyl alpha-oxo-3-(2-nitro-4,5dichlorophenyl) propanoate. To a suspension of potassium (49.2 g, 1.26 mol) in anhydrous diethyl ether (500 ml), a solution of absolute EtOH (319 ml) and anhydrous diethyl ether (260 ml) was added dropwise under nitrogen during a period of four hours. The resulting solution was diluted with anhydrous diethyl ether (1200 mL) and then diethyl oxalate (171 ml, 1.26 mol) was added dropwise in about 30 minutes. To the resulting yellow mixture, a solution of 2-nitro-4,5-dichlorotoluene (260 g, 1.26 mmol), prepared as described by Cohen and Dakin in *J. Chem. Soc.*, 79, 1133, in anhydrous diethyl ether (450 ml) was added dropwise in one hour at RT. Stirring was continued for additional three hours and the dark-brown mixture was settled at RT for two days. The potassium salt was collected by suction and dried to give a dark-brown powder. This was suspended in a mixture of water (400 ml) and ethyl acetate (400 ml), then acidified with 10% HCl. The organic phase was washed with brine, aqueous sat. $NaHCO_3$ and again brine, then it was dried with $MgSO_4$. Evaporation produced 239 g of title compound (781 mmol, yield 62.0%) as a light brown solid that was used as such for the next step, m.p.=92–94° C.

Preparation 2

Ethyl 5,6-dichloroindole-2-carboxylate. A mixture of ethyl alpha-oxo-3-(2-nitro-4,5-dichlorophenyl)propanoate (200 g, 653 mmol) and iron powder (320 g, 5.75 mol) in EtOH/AcOH 1/1 (2.5 l) was refluxed for two hours. After cooling, the resulting mixture was evaporated under vacuum and the solid residue was dissolved in THF (4 l). The solid residue was filtered on Fluosil and then washed with additional THF (2 l). The pooled organic phases were concentrated to give a dark residue (203 g). This was treated with AcOEt/$CH_2Cl_2$ and the remaining solid was filtered off. Evaporation produced 120 g of title compound (465 mmol, yield 71.2%) that was used as such for the next step, m.p.=215–218° C.

Preparation 3

5,6-Dichloroindole-2-methanol. To an ice cold stirred 1M solution of $LiAlH_4$ in anhydrous THF (800 ml, 800 mmol) under argon, ethyl 5,6-dichloroindole-2-carboxylate (118 g, 457 mmol), dissolved in anhydrous THF (1 l), was added dropwise while keeping the temperature below 5°. Stirring at 0° was continued for one hour, then the reaction was quenched with water (35 ml), 15% aq. NaOH (35 ml) and water (70 ml). The mixture was filtered on a Celite pad and washed with THF (2×500 ml). The organic phase was dried ($MgSO_4$) and concentrated to give a residue (80 g) that was chromatographed with AcOEt/n-heptane ½ to give 52.0 g of pure title compound (241 mmol, yield 52.7%) as an oil.

Preparation 4

5,6-Dichloroindole-2-carboxaldehyde. A solution of 5,6-dichloroindole-2-methanol (43 g, 199 mmol) in diethyl ether (1.3 l) was treated with activated $MnO_2$ (64 g, 730 mmol) and stirred for 15 hours at room temperature. Additional $MnO_2$ (20 g, 230 mmol) was added and stirring continued for 5 h. The suspension was filtered on a Celite pad, then the pad was washed with diethyl ether and warm acetone. The pooled organic phases were concentrated to give 38.5 g of the title compound (180 mmol, yield 90.4%) that was used as such in the next step, m.p.=207–208° C.

Preparation 5

Method A). Ethyl (E)-3-(5,6-dichloroindol-2-yl)-2-propenoate. 5,6-Dichloro indole-2-carboxaldehyde (35 g, 164 mmol) was dissolved in toluene (1.5 l) under argon, then (ethoxycarbonylmethylene)triphenylphosphorane (60 g, 176 mmol) was added and the solution was refluxed for 3 h. The solvent was evaporated under reduced pressure and the residue chromatographed on silicagel with AcOEt/n-heptane ¼ to give 28.0 g of pure title compound, m.p.=188–190° C. (yield 60.1%).

Method B). Ethyl (E)-3-(5,6-dichloroindol-2-yl)-2-propenoate. To a solution of triethyphosphonoacetate (32.9 g, 147 mmol) in THF (150 ml), NaH (5.95, 148 mmol) was added portionwise under nitrogen maintaining the temperature between 0–5° C. in 30 min. After reaching room temperature, 5,6-dichloro-1H-indol-2-carboxaldehyde (29 g, 135.5 mmol), dissolved in THF (200 ml), was added dropwise maintaining the internal temperature around 20° C. (about 1 h). The solvent was evaporated under reduced pressure and the residue was treated with $H_2O$ (200 ml) and EtOAc (500 ml). The organic layer was washed with brine, dried over $Na_2SO_4$ and evaporated to dryness obtaining a residue that was triturated with hexane, filtered and dried under vacuum affording 34.5 g of the title compound, m.p.=188–190° C. (yield=89.6%).

Preparation 6

(E)-3-(5,6-Dichloroindol-2-yl)-2-propen-1-ol. To a solution of ethyl (E)-3-(5,6-dichloroindol-2-yl)-2-propenoate (28 g, 98.5 mmol) in dry THF (500 ml) stirred under argon at −20° DIBAL (1M solution in hexane, 200 mmol) was added dropwise while keeping the temperature below −20°. The stirring was continued for one hour, then the reaction was quenched with water (70 m). After warming to RT diethyl ether (350 m) was added and the suspension was filtered on a Celite pad. The pad was washed with diethyl ether (3×100 ml), then the pooled organic phase was dried ($MgSO_4$) and evaporated to give 23.85 g of the title compound (98.5 mmol, yield 100%) that was used as such in the next step.

Preparation 7

(E)-3-(5,6-Dichloroindol-2-yl)-2-propenaldehyde. To a solution of (E) 3-(5,6-dichloroindol-2-yl)-2-propen-1-ol (23.8 g, 98.3 mmol) in diethyl ether (800 ml) activated $MnO_2$ (71 g, 8.76 mol) and NaCl (60 g) were added and the resulting suspension stirred for one day at RT. It was then filtered on a Celite pad repeatedly washed with AcOEt and the organic phase dried ($MgSO_4$) and evaporated to give 21.0 g of the title compound (87.5 mmol, yield 89.0%) that was used as such in the next step.

Preparation 8

Methyl (2Z,4E)-5-(5,6-dichloroindol-2-yl)-2-methoxy-2,4-pentadienoate. A solution of (E) 3-(5,6-dichloroindol-2-yl)-2-propenaldehyde (15 g, 62.5 mmol), methyl 2-methoxy-2-(triphenylphosphonium)acetate bromide (31 g, 69.6 mmol) and DBU (10.5 mL, 70.1 mmol) was refluxed for 4 h. The solvent was evaporated and the crude chromatographed on silicagel with AcOEt/n-heptane ¼ to give 14.5 g of pure title compound (44.5 mmol, yield 71.1%) after trituration with diisopropyl ether, m.p.=203–204° C.

Preparation 9

(2Z,4E)-5-(5,6-Dichloroindol-2-yl)-2-methoxy-2,4-pentadienoic acid. A suspension of methyl (2Z,4E)-5-(5,6-dichloroindol-2-yl)-2-methoxy-2,4-pentadienoate (10 g, 30.7 mmol) and KOH (3.6 g, 64.2 mmol) in EtOH/water ⅓ (460 ml) was refluxed for 3 h. The suspension after cooling to RT was poured into water (1.5 l), it was acidified with 2N HCl and extracted with AcOEt (2×1 l). The organic phase was washed with water and dried ($MgSO_4$), then concentrated and the residue taken up with $CH_2Cl_2$. Filtration and drying in the oven at 50° produced 9.5 g of pure title compound (30.4 mmol, yield 99.1%), m.p.=249–250° C.

$^1$H-NMR (DMSO-$d_6$): 11.81 (bs, 1H); 7.77 (s, 1H); 7.53 (s, 1H); 7.20 (dd, 1H); 6.95 (d, 1H); 6.84 (d, 1H); 6.61 (s, 1H); 3.74 (s, 3H)

Preparation 10

1,2,2,6,6-Pentamethyl-4-piperidone hydroiodide. A solution of 2,2,6,6-tetramethyl-4-piperidone monohydrate (40 g, 23.1 mmol) and methyl iodide (98.31 g, 69.3 mmol) in isopropyl alcohol (25 mL) was stirred at RT for 48 hours. The resulting suspension was filtered, the solid residue was dried and recrystallized from MeOH. After filtration and repeated washings with MeOH the solid was dried giving pure title compound (31.6 g, 10.6 mmol, yield 46.0%) as pale brown crystals.

Preparation 11

1,2,2,6,6-Pentamethyl-4-piperidone oxime. A suspension of 1,2,2,6,6-pentamethyl-4-piperidone hydroiodide (3 g, 10.1 mmol) and hydroxylamine hydrochloride (980 mg, 14 mmol) in water (6 ml) was stirred at RT for 15 minutes. Solid NaOH was added until basic pH and thickening of the suspension. Water (3 ml) was added and stirring at RT was continued overnight. The suspension was filtered and the solid washed with water (few ml) and dried. The solid was then dissolved in $Et_2O$, the solution was dried ($MgSO_4$) and concentrated to give after drying pure title compound (1.55 g, 8.41 mmol, yield 83.3%) as white crystals.

Preparation 12

4-Amino-1,2,2,6,6-pentamethyl-4-piperidine. $LiAlH_4$ (925 mg, 24.4 mmol) was added under stirring at 0° under Ar to anhydrous THF (100 ml), followed by 1,2,2,6,6-pentamethyl-4-piperidone oxime (1.50 g, 8.14 mmol). The suspension was refluxed for 2 hours, then cooled to RT and stirred overnight. After cooling to 0° water (0.9 ml), 15% aq. NaOH (0.9 ml) and water (2.8 ml) were carefully added dropwise. The suspension was stirred for 15 min at RT, then $MgSO_4$ was added and stirring continued for 30 minutes. After filtration, the liquid was concentrated and the oily residue chromatographed on silicagel ($CH_2Cl_2$/MeOH/aq.$NH_3$ 95/5/1). The collected fractions were pooled and concentrated to give pure title compound (750 mg, 4.40 mmol, yield 54.1%) as a yellow oil.

Preparation 13

(2Z,4E)-5-(Indol-2-yl)-2-methoxy-2,4-pentadienoic acid was prepared from 2-indolecarbaldehyde (*Heterocycles*, 1984, 22, 1211) using the reaction sequence described in Preparations 5–9. m.p.=189–190° C.

Preparation 14

Ethyl 5-trifluoromethyl-2-indolecarboxylate. 5-Trifluoromethylphenylhydrazine (5 g, 28.4 mmol) was treated with ethyl pyruvate (3.3 ml, 30 mmol) in ethanol (15 ml) giving, after filtration, 5.4 g of the corresponding phenylhydrazone as a white powder, m.p.=134–137° C. This compound (5.4 g, 19.7 mmol) was refluxed for 3 h in toluene (150 ml) in the presence of anhydrous p-toluensulfonic acid (6 g, 34.8 mmol) obtaining 0.9 g (18%) of the title compound as a yellow powder, m.p.=153–154° C.

Preparation 15

(2Z,4E)-5-(5-Trifluoromethylindol-2-yl)-2-methoxy-2,4-pentadienoic acid was prepared from ethyl 5-trifluoromethyl-2-indolecarboxylate using the reaction sequence described in Preparations 3–9. m.p.=191–193° C.

Preparation 16

Ethyl 5-bromo-2-indolecarboxylate was prepared from 5-bromophenylhydrazine and ethyl piruvate using the procedure described in Preparation 14, m.p.=160–164° C.

Preparation 17

(2Z,4E)-5-(5-Bromoindol-2-yl)-2-methoxy-2,4-pentadienoic acid was prepared from ethyl 5-bromo-2-indolecarboxylate using the reaction sequence described in Preparations 3–9, m.p.=208–210° C.

Preparation 18

2,6-Dimethyl-4-(2-pyrimidinyl)piperazine dihydrochloride A solution of 1.71 g (15 mmol) of 2,6-dimethylpiperazine and 1.14 g (10 mmol) of 2-chloropyrimidine in 25 ml ethanol was refluxed for 16 hours. The reaction mixture was concentrated under reduced pressure, dissolved in 25 ml of water and extracted twice with 50 ml of methylene chloride. The organic phase was dried over $MgSO_4$ and concentrated under reduced pressure. The residue was dissolved in acetonitrile and treated with a solution of anhydrous HCl in ethanol. The salt was filtered and dried in vacuo to afford 1.70 g of the title compound.

Preparation 19

3-[2,6-Dimethyl-4-(2-pyrimidinyl)piperazin-1-yl]propylamide. A mixture of 1.1 g (4.1 mmol) of 2,6-dimethyl-4-(2-pyrimidinyl)piperazine dihydrochloride, 0.45 g (4.1 mmol) of 3-chloropropionamide, 3 g of 30% KF on Clarcel® in 25 ml acetonitrile was heated for 72 hours at 150° C. in a close vessel. After cooling to room temperature the mixture was filtered over a filtration aid and concentrated under reduced pressure.

The residue was dissolved in water, alkalinised with aqueous 1N NaOH and extracted twice with 25 ml methylene chloride. The organic phase was dried over $MgSO_4$ and concentrated under reduced pressure. The residue was then purified by chromatography on silicagel (AcOEt, EtOH, $NH_4OH$: 45, 5, 1) to afford 0.2 g of the title compound, mp.=125° C.

Preparation 20

3-[2,6-Dimethyl-4-(2-pyrimidinyl)piperazin-1-yl]propylamine. 50 mg (1.54 mmol) of $LiAlH_4$ were added to a solution of 0.2 g (0.77 mmol) of 3-[2,6-dimethyl-4-(2-pyrimidinyl)piperazin-1-yl]propylamide in 5 ml of diethylether and 5 ml of THF. The mixture was stirred one hour at room temperature and one additional hour at reflux, then the reaction was quenched by successive addition of 50 ul of water, 50 ul of 15% aqueous NaOH and 3×50 ul water. The mixture was diluted with diethyl ether, filtered, dried over $MgSO_4$ and concentrated under reduced pressure. The residue was purified by column chromatography on silicagel ($CH_2Cl_2$, EtOH, $NH_4OH$: 45, 5, 1) to afford 0.037 g of the title compound.

Preparation 21

3-[4-(2,6-Dimethylphenyl)piperazin-1-yl]propylamine. 4-(2,6-Dimethylphenyl) piperazine (1 g, 5.23 mmol) in MeOH (10 ml) was cooled to 0° and 0.305 g (5.73 mmol) of acrilonitrile was added. The reaction was stirred overnight at room temperature and evaporated under vacuum affording 1 g of crude 3-[4-(2,6-dimethylphenyl)piperazin-1-yl] propionitrile as a waxy solid. This compound was dissolved in MeOH (60 ml), 2 ml 37% HCl and hydrogenated under pressure (40 psi) with 0.2 g of 10% Pd\C. The reaction was filtered and evaporated to dryness obtaining 1 g of the title compound, as a hydrochloride salt, that was used without further purification for the following reaction.

EXAMPLE 1

(2Z,4E)-5-(5,6-Dichloro-1H-indol-2-yl)-2-methoxy-N-(1,2,2,6,6-pentamethyl piperidin-4-yl)-2,4-pentadienamide. A solution of (2Z,4E)-5-(5,6-dichloro-1H-indol-2-yl)-2-methoxy-2,4-pentadienoic acid (736 mg, 3.65 mmol), 4-amino-1,2,2,6,6-pentamethylpiperidine (620 mg, 3.65 mmol), 1-hydroxy-7-azabenzotriazole hydrate (474.5 mg, 3.65 mmol) and 1-(3-dimethylaminopropyl)-3-ethylcarbodiimide hydrochloride (693.5 mg, 3.65 mmol) in DMF (2 ml) was stirred at RT overnight. The solution was poured into brine (20 ml) and repeatedly extracted with EtOAc. The organic phase was washed with 5% aq. $CaCO_3$, dried ($MgSO_4$) and evaporated under vacuum. The residue was chromatographed on silica gel using ethyl acetate-:methanol:aq. ammonia (32%) 90:10:2 as eluent mixture. The collected fractions produced the pure title compound (0.8, yield 73%) as yellow crystals, m.p.=212° C.

$^1$H-NMR (200 MHz, DMSO-$d_6$): 1.02 (s, 6H); 1.08 (s, 6H); 1.44(t, 2H); 1.62 (m, 2H); 2.18 (s, 3H); 3.70 (s, 3H); 4.07 (m, 1H); 6.6 (m, 2H); 6.84 (d, 1H); 7.14 (dd, 1H); 7.51 (s, 1H); 7.75 (s, 1H); 7.91 (d, 1H); 11.74 (s, 1H, exch with D2O)

Two other isomers were isolated from the column chromatography:

(2E,4E)-5-(5,6-Dichloro-1H-indol-2-yl)-2-methoxy-N-(1,2,2,6,6-pentamethyl piperidin-4-yl)-2,4-pentadienamide $^1$H-NMR (200 MHz, THF-$d_8$,): 10.76 (s br, 1H); 8.19 (dd, 1H); 7.54 (s, 1H); 7.40 (s, 1H); 6.93 (d br, 1H); 6.51 (d, 1H); 6.32 (d, 1H); 5.92 (d, 1H); 4.25–4.12 (m, 1H); 3.70 (s, 3H); 2.25 (s, 3H); 1.72 (m, 2H); 1.32 (dd, 2H); 1.10 (s, 12H).

(2Z,4Z)-5-(5,6-Dichloro-1H-indol-2yl)-2-methoxy-N-(1,2,2,6,6-pentamethyl piperidin-4-yl)-2,4-pentadienamide $^1$H-NMR (200 MHz, THF-$d_8$,): 10.48 (s br, 1H); 7.58 (s, 1H); 7.44 (s, 1H); 7.22 (d, 1H); 6.99 (d br, 1H); 6.61 (s br, 1H); 6.59 (dd, 1H); 6.42 (d, 1H); 4.25–4.12 (m, 1H); 3.75 (s, 3H); 2.28 (s, 3H); 1.72 (m, 2H); 1.33 (dd, 2H); 1.11 (s, 12H).

The following compounds were prepared according to the procedure of Example 1

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 2 | (2Z,4E)-5-(5,6-Dichloro-1H-indol-2-yl)-2-methoxy-N-(6-ethoxy-pyridin-3-yl)-2,4-pentadienamide | 5-methyl-2-OC₂H₅-pyridin-3-yl | H | Me | H | H | H | H | 5Cl | 6Cl | H | 273 | ¹H NMR(DMSO-d₆): 1.30(t, 3H); 3.82(s, 3H); 4.27(q, 2H); 6.62(s, 1H); 6.77–6.98(m, 3H); 7.25(dd, 1H); 7.53(s, 1H); 7.77(s, 1H); 8.04(dd, 1H); 8.49(d, 1H); 10.04(s, 1H, exch with D₂O); 11.81(s, 1H, exch with D₂O). |
| 3 | (2Z,4E)-N-(5-Chloropyridin-2-yl)-5-(5,6-dichloro-1H-indol-3-yl)-2-methoxy-2,4-pentadienamide | 5-Cl-pyridin-2-yl | H | Me | H | H | H | H | 5Cl | 6Cl | H | 284 dec. | ¹H NMR(DMSO-d₆): 3.84(s, 3H); 6.64(s, 1H); 6.90(d, 1H); 7.00(d, 1H); 7.25(dd, 1H); 7.54(s, 1H); 7.77(s, 1H); 7.97(dd, 1H); 8.16(d, 1H); 8.43(d, 1H); 10.13(s, 1H, exch with D₂O); 11.82(s, 1H, exch with D₂O). |
| 4 | (2Z,4E)-5-(5,6-Dichloro-1H-indol-2-yl)-2-methoxy-N-[(2,4-dimethoxy)pyridin-3-yl]-2,4-pentadienamide | 2,4-dimethoxy-pyridin-3-yl | H | Me | H | H | H | H | 5Cl | 6Cl | H | 1.75 | ¹H NMR(DMSO-d₆): 3.42(s, 3H); 3.81(s, 6H); 6.33(d, 1H); 6.59(s, 1H); 6.67(d, 1H); 6.87(d, 1H); 7.22(dd, 1H); 7.53(s, 1H); 7.73(m, 2H); 8.77(s, 1H, exch with D₂O); 11.83(s, 1H, exch with D₂O). |
| 5 | (2Z,4E)-5-(5,6-Dichloro-1H-indol-2-yl)-2-methoxy-N-(2-methoxy-pyrimidin-5-yl)-2,4-pentadienamide | 2-OMe-pyrimidin-5-yl | H | Me | H | H | H | H | 5Cl | 6Cl | H | 290–291 | ¹H NMR(DMSO-d₆): 3.84(s, 3H); 3.90(s, 3H); 6.64(s, 1H); 6.88(d, 1H); 6.96(d, 1H); 7.25(dd, 1H); 7.54(s, 1H); 7.77(s, 1H); 8.91(s, 2H); 10.25(s, 1H, exch with D₂O); 11.82(s, 1H, exch with D₂O). |
| 6 | (2Z,4E)-5-(5,6-Dichloro-1H-indol-2-yl)-2-methoxy-N-(5-methoxy-pyridin-3-yl)-2,4-pentadienamide | 5-OMe-pyridin-3-yl | H | Me | H | H | H | H | 5Cl | 6Cl | H | 235–236 | ¹H NMR(DMSO-d₆): 3.84(s, 3H); 3.85(s, 3H); 6.64(s, 1H); 6.87(d, 1H); 6.97(dd, 1H); 7.27(dd, 1H); 7.54(s, 1H); 7.77(s, 1H); 7.96(m, 1H); 8.11(d, 1H); 8.67(d, 1H); 10.27(s, 1H, exch with D₂O); 11.84(s, 1H, exch with D₂O). |

-continued

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 7 | (2Z,4E)-5-(5,6-Dichloro-1H-indol-2-yl)-2-methoxy-N-(3-(4-benzoylpiperazin-1-yl)propyl]-2,4-pentadienamide | benzoylpiperazinyl-butyl | H | Me | H | H | H | H | 5Cl | 6Cl | H | 232 | $^1$H NMR(DMSO-d$_6$): 1.64(m, 2H); 2.35(m, 6H); 3.19–3.26(m 4H); 3.44–3.62(m, 2H); 3.72(s, 3H); 6.58(s, 1H); 6.65(d, 1H); 6.85(d, 1H); 7.17(dd, 1H); 7.36–7.46(m, 5H); 7.51(s, 1H); 7.75(s, 1H); 8.25(t, 1H, exch with D$_2$O); 11.75(s, 1H, exch with D$_2$O) |
| 8 | (2Z,4E)-5-(5,6-Dichloro-1H-indol-2-yl)-N-[6-(2-hydroxyethoxy)-pyridin-3-yl]-2-methoxy-2,4-pentadienamide | 5-methyl-2-(2-hydroxyethoxy)pyridyl | H | Me | H | H | H | H | 5Cl | 6Cl | H | 228 dec. | $^1$H NMR(DMSO-d$_6$): 3.70(m, 2H); 3.82(s, 3H); 4.22(t, 2H); 4.82(m, 1H, exch with D$_2$O); 6.62(s, 1H); 6.80–6.98(m, 3H); 7.24(dd, 1H); 7.53(s, 1H); 7.77(s, 1H); 8.04(m, 1H); 8.49(s, 1H); 10.04(s, 1H, exch with D$_2$O) 11.80(s, 1H, exch with D$_2$O) |
| 9 | (2Z,4E)-5-(5,6-Dichloro-1H-indol-2-yl)-2-methoxy-N-(2-pyridyloxy-5-pyridyl)-2,4-pentadienamide hydrochloride | 5-(pyridin-3-yloxy)pyridyl | H | Me | H | H | H | H | 5Cl | 6Cl | H | 208–210 | $^1$H NMR(DMSO-d$_6$): 11.85(s, 1H); 10.21(s, 1H); 8.64(d, 1H); 8.53(s, 1H); 8.52(m, 1H); 8.29(dd, 1H); 7.89(m, 1H); 7.76(s, 1H); 7.67(dd, 1H); 7.52(s, 1H); 7.27(dd, 1H); 7.20(d, 1H); 6.95(d, 1H); 6.85(s, 1H); 6.64(s, 1H); 3.82(s, 3H) |
| 10 | (S,2Z,4E)-5-(5,6-Dichloroindol-2-yl)-N-[2-(1-carbethoxy)-ethoxy-5-pyridyl]-2-methoxy-2,4-pentadienamide | 5-methyl-2-[(1-carbethoxy)ethoxy]pyridyl | H | Me | H | H | H | H | 5Cl | 6Cl | H | 228–230 | $^1$H NMR(DMSO-d$_6$): 11.75(s, 1H); 10.00(s, 1H); 8.42(d, 1H); 8.06(dd, 1H); 7.77(s, 1H); 7.52(s, 1H); 7.23(dd, 1H); 6.93(d, 1H); 6.82(d, 1H); 6.62(s, 1H); 5.19(q, 1H); 4.11(q, 2H); 3.81(s, 3H); 1.50(d, 3H); 1.16(t, 3H) |
| 11 | (S,2Z,4E)-5-(5,6-Dichloroindol-2-yl)-N-[2-(1-carboxy)ethoxy-5-pyridyl]-2-methoxy-2,4-pentadienamide | 5-methyl-2-[(1-carboxy)ethoxy]pyridyl | H | Me | H | H | H | H | 5Cl | 6Cl | H | 239–240 | $^1$H NMR(DMSO-d$_6$): 11.80(s, 1H); 10.00(s, 1H); 8.42(d, 1H); 8.05(dd, 1H); 7.76(s, 1H); 7.52(s, 1H); 7.25(dd, 1H); 6.94(d, 1H); 6.87(d, 1H); 6.81(d, 1H); 6.61(s, 1H); 5.18(q, 1H); 3.82(s, 3H); 1.50(d, 3H) |

-continued

| Ex. No | Name | Rs | Rt | R1 | R2 | R3 | R4 | Ra | R6 | R7 | R8 | MP. (°C) | N.M.R. |
|---|---|---|---|---|---|---|---|---|---|---|---|---|---|
| 12 | (2Z,4E)-5-(5,6-Dichloro-1H-indol-2-yl)-2-methoxy-N-[6-(1-methyl-ethoxy)pyridin-3-yl]-2,4-pentadienamide | (6-isopropoxy-5-methylpyridin-3-yl) | H | Me | H | H | H | H | 5Cl | 6Cl | H | 263 dec. | $^1$H NMR(DMSO-d$_6$): 1.28(s, 6H); 3.82(s, 3H); 5.19(m, 1H); 6.62(s, 1H); 6.72–6.98(m, 3H); 7.24(dd, 1H); 7.54(s, 1H); 7.77(s, 1H); 8.00(dd, 1H); 8.50(d, 1H); 10.03(s, 1H, exch with D$_2$O); 11.81(s, 1H, exch with D$_2$O) |
| 13 | (2Z,4E)-5-(5,6-Dichloro-1H-indol-2-yl)-2-methoxy-N-(6-dimethylaminopyridin-3-yl)-2,4-pentadienamide | (6-dimethylamino-5-methylpyridin-3-yl) | H | Me | H | H | H | H | 5Cl | 6Cl | H | 260–290 | $^1$H NMR(DMSO-d$_6$): 3.00(s, 6H); 3.82(s, 3H); 6.61(s, 1H); 6.64(d, 1H); 6.78(d, 1H); 6.91(d, 1H); 7.23(dd, 1H); 7.53(s, 1H); 7.76(s, 1H); 7.85 dd, 1H); 8.41(d, 1H); 9.81(s, 1H, exch with D$_2$O); 11.78(s, 1H, exch with D$_2$O) |
| 14 | (2Z,4E)-5-(5,6-Dichloro-1H-indol-2-yl)-2-methoxy-N-(1-azabicyclo-[3.3.1]nonan-4 beta-yl)-2,4-pentadienamide | (1-azabicyclo[3.3.1]nonan-4β-yl) | H | Me | H | H | H | H | 5Cl | 6Cl | H | 230 | $^1$H NMR(DMSO-d$_6$): 1.10–2.25(bm, 7H), 2.60–3.05(m, 6H); 3.73(s, 3H); 4.15(m, 1H); 6.57(s, 1H); 6.59(d, 1H); 6.85(d, 1H); 7.17(dd, 1H); 7.51(s, 1H); 7.75(s, 1H); 8.06(d, 1H, exch with D$_2$O); 11.76(s, 1H, exch with D$_2$O) |
| 15 | (2Z,4E)-5-(5,6-Dichloro-1H-indol-2-yl)-2-methoxy-N-(9-methyl-9-azabicyclo[3.3.1]nonan-3 alpha-yl)-2,4-pentadienamide | (9-methyl-9-azabicyclo[3.3.1]nonan-3α-yl) | H | Me | H | H | H | H | 5Cl | 6Cl | H | 293 | $^1$H NMR(DMSO-d$_6$): 0.86–2.15(bm, 10); 2.38(s, 3H); 2.84–3.04(m, 2H); 3.71(s, 3H); 4.20(m, 1H); 6.63(d, 1H); 6.84(d, 1H); 7.17(dd, 1H); 7.51(s, 1H); 7.75(s, 1H); 7.87(d, 1H, exch with D$_2$O); 11.75(s, 1H,exch with D$_2$O) |
| 16 | (2Z,4E)-5-(5,6-Dichloro-1H-indol-2-yl)-2-methoxy-N-(8-methyl-8-azabicyclo[3.2.1]oct-3alpha-yl)-2,4-pentadienamide | (8-methyl-8-azabicyclo[3.2.1]oct-3α-yl) | H | Me | H | H | H | H | 5Cl | 6Cl | H | 262 | $^1$H NMR(DMSO-d$_6$): 1.98–2.46(m, 8H); 2.59(s, 3H); 3.76(s, 3H); 3.78(m, 1H); 6.58(s, 1H); 6.60(d, 1H); 6.88(d, 1H); 7.21(dd, 1H); 7.53(s, 1H); 7.75(s, 1H); 7.95(m, 1H, exch with D$_2$O); 11.89(s, 1H, exch with D$_2$O) |

| Ex. No | Name | Rs | Rt | R1 | R2 | R3 | R4 | Ra | R6 | R7 | R8 | MP. (°C.) | N.M.R. |
|---|---|---|---|---|---|---|---|---|---|---|---|---|---|
| 17 | (2Z,4E)-5-(5,6-Dichloro-1H-indol-2-yl)-N-(6-(2-methoxyethoxy)-pyridin-3-yl]-2-methoxy-2,4-pentadienamide | 5-methyl-2-(2-methoxyethoxy)pyridin-3-yl | H | Me | H | H | H | H | 5Cl | 6Cl | H | 233 dec | $^1$H NMR(DMSO-d$_6$); 11.80(s, 1H, exch with D$_2$O); 10.01(s, 1H, exch with D$_2$O); 8.50(d, 1H); 8.04(dd, 1H); 7.77(s, 1H); 7.54(s, 1H); 7.24(dd, 1H); 6.81–6.99(m, 3H); 6.62(s, 1H); 4.34(t, 2H); 3.82(s, 3H); 3.64(t, 2H); 3.29(s, 3H). |
| 18 | (2Z,4E)-5-[2-(1-Carboxymethyl-5,6-dichloro)indolyl]-2-methoxy-N-[5-(2-methoxypyridinyl)]-2,4-pentadienamide | 2-methoxy-5-pyridyl | H | Me | H | H | H | H | 5Cl | 6Cl | CH2—COOH | >250 | $^1$H NMR(DMSO-d$_6$); 10.04(s,1H); 9.01(d, 1H); 8.04(dd, 1H); 7.82(s, 1H); 7.78(s, 1H); 7.60(d, 1H); 7.40(s, 1H); 7.26(dd, 1H); 6.86(d, 1H); 6.82(d, 1H); 5.18(s, 2H); 3.82(s, 3H). |
| 19 | (2Z,4E)-5-(5,6-Dichloro-1H-indol-2-yl)-N-[6-(2-diethylaminoethoxy)pyridin-3-yl]-2-methoxy-2,4-pentadienamide hydrochloride | 6-(2-diethylaminoethoxy)pyridin-3-yl | H | Me | H | H | H | H | 5Cl | 6Cl | H | 201–204 | $^1$H NMR(DMSO-d$_6$); 10.10(s, 1H); 9.80(s br, 1H); 8.55(d, 1H); 8.11(dd, 1H); 7.76(s, 1H); 7.54(s, 1H); 7.26(dd, 1H); 6.95(d, 1H); 6.90(d, 1H); 6.82(d, 1H); 6.61(s, 1H); 4.59(t, 2H); 3.83(s, 3H); 3.50(t, 2H); 3.20(m, 4H); 1.22(t, 6H). |
| 20 | (2Z,4E)-5-(5,6-Dichloro-1H-indol-2-yl)-N-(1-methylethyl-6-oxopyridin-3-yl)-2-methoxy-2,4-pentadienamide | 1-(1-methylethyl)-6-oxo-1,6-dihydropyridin-3-yl | H | Me | H | H | H | H | 5Cl | 6Cl | H | 165–168 dec. | $^1$H NMR(DMSO-d$_6$); 11.81(s, 1H, exch with D$_2$O); 9.86(s, 1H, exch with D$_2$O); 8.21(d, 1H); 7.77(s, 1H); 7.68(dd, 1H); 7.54(s, 1H); 7.23(dd, 1H); 6.92(d, 1H); 6.81(d, 1H); 6.62(s, 1H); 6.40(d, 1H); 5.07(m, 1H); 3.81(s, 3H); 1.28(d, 6H). |
| 21 | (2Z,4E)-5-(1H-Indol-2-yl)-2-methoxy-N-[4-(2,2,5,6-tetramethyl)-piperidinyl]-2,4-pentadienamide hydrochloride | 2,2,5,6-tetramethylpiperidin-4-yl | H | Me | H | H | H | H | H | H | H | >250 | $^1$H NMR(DMSO-d$_6$); 11.41(s, 1H); 9.09(d br, 1H); 8.19(d, 1H); 8.01(d br, 1H); 7.49(d, 1H); 7.32(d, 1H); 7.12(dd, 1H); 7.11(dd, 1H); 6.97(dd, 1H); 6.85(d, 1H); 6.65(d, 1H); 6.56(s, 1H); 4.22(m, 1H); 3.71(s, 3H); 1.85(dd, 1H); 1.65(dd, 1H); 1.43(s, 6H); 1.41(s, 6H). |

-continued

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 22 | (2Z,4E)-5-(5,6-Dichloro-3-ethyl-1H-indol-2-yl)-2-methoxy-N-[4-(2,2,6,6-tetramethyl)piperidinyl]-2,4-pentadienamide hydrochloride | 2,2,6,6-tetramethyl-4-piperidinyl (NH) | H | Me | H | H | H | Et | 5Cl | 6Cl | H | >250 | $^1$H NMR(DMSO-d$_6$): 11.52(s, 1H); 9.00(d br, 1H); 8.20(d, 1H); 7.99(d br, 1H); 7.75(s, 1H); 7.46(s, 1H); 7.13(dd, 1H); 6.98(d, 1H); 6.70(d, 1H); 4.12(m, 1H); 3.71(s, 3H); 2.78(m, 2H); 1.85(d br, 2H); 1.61(dd br, 2H); 1.44(s, 6H); 1.40(s, 6H); 1.13(t, 3H). |
| 23 | (2Z,4E)-5-(5,6-Dichloro-1H-indol-2-yl)-N-[6-(2-dimethylaminoethylamino)-pyrid-3-yl]-2-methoxy-2,4-pentadienamide | 6-(2-dimethylaminoethylamino)pyrid-3-yl (5-methyl) | H | Me | H | H | H | H | 5Cl | 6Cl | H | >250 | $^1$H NMR(DMSO-d$_6$ + TFA): 11.86(s, 1H); 10.32(s, 1H); 10.05(s br, 1H); 8.55(d, 1H); 8.26(dd, 1H); 7.75(s, 1H); 7.53(s, 1H); 7.26(dd, 1H); 7.16(d, 1H); 6.96(d, 1H); 6.88(d, 1H); 6.62(s, 1H); 3.82(s, 3H); 3.79(t, 2H); 3.36(t br, 2H); 2.85(s, 6H). |
| 24 | (2Z,4E)-5-[(5,6-Dichloro-1H-indol-2-yl)-2-methoxy-N-[3-piperazin-1-yl)-propyl]-2,4-pentadienamide | 3-(piperazin-1-yl)propyl | H | Me | H | H | H | H | 5Cl | 6Cl | H | 200 | $^1$H NMR(DMSO-d$_6$): 1.61(m, 2H); 2.19–2.43(m, 6H); 2.80(m, 4H); 3.20(m, 2H); 3.72(s, 3H); 6.57(s, 1H); 6.64(d, 1H); 6.85(d, 1H); 7.17(dd, 1H); 7.52(s, 1H); 7.75(s, 1H); 8.27(t, 1H, exch with D$_2$O); 11.79(s, 1H, exch with D$_2$O). |
| 25 | (2Z,4E)-5-(5,6-Dichloro-1-methylindol-2-yl)-2-methoxy-N-[4-(2,2,6,6-tetramethyl)piperidinyl]-2,4-pentadienamide | 2,2,6,6-tetramethyl-4-piperidinyl (NH) | H | Me | H | H | H | H | 5Cl | 6Cl | Me | 210–213 | $^1$H NMR(DMSO): 7.90(m br, 1H); 7.80(s, 1H); 7.74(s, 1H); 7.19(dd, 1H); 7.05(d, 1H); 6.93(s, 1H); 6.67(d, 1H); 4.19(m br, 1H); 3.79(s, 3H); 3.71(s, 3H); 1.65(m, 2H); 1.20(m, 2H); 1.20(s, 6H); 1.09(s, 6H). |
| 26 | (2Z,4E)-5-(5-Trifluoromethylindol-2-yl)-2-methoxy-N-[4-(2,2,6,6-tetramethyl)piperidinyl]-2,4-pentadienamide hydrochloride | 2,2,6,6-tetramethyl-4-piperidinyl (NH) | H | Me | H | H | H | H | 5CF$_3$ | H | H | >250 | $^1$H NMR(DMSO-d$_6$): 11.90(s, 1H); 8.99(d br, 1H); 8.23(d, 1H); 7.96(d br, 1H); 7.89(s, 1H); 7.50(d, 1H); 7.49(d, 1H); 7.21(dd, 1H); 6.90(d, 1H); 6.72(s, 1H); 6.64(d, 1H); 4.23(m, 1H); 3.71(s, 3H); 1.88(d br, 2H); 1.62(dd br, 2H); 1.42(s, 6H); 1.40(s, 6H). |

-continued

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 27 | (2Z,4E)-5-(5,6-Dichloro-1H-indol-2-yl)-2-methoxy-N-(3,7-dimethyl-3,7-diazabicyclo[3.3.1]nonan-9-yl)-2,4-pentadienamide | N-Me bicyclic (3,7-dimethyl-3,7-diazabicyclo[3.3.1]nonan-9-yl) | H | Me | H | H | H | H | 5Cl | 6Cl | H | 200 | $^1$H NMR(DMSO-d$_6$): 2.26(m, 2H); 2.39(s, 3H); 2.53(s, 3H); 2.66–3.33(m, 8H); 3.76(s, 3H); 3.88(m, 1H); 6.58(s, 1H); 6.64(d, 1H); 6.87(d, 1H); 7.20(dd, 1H); 7.53(s, 1H); 7.75(s, 1H); 8.12(d, 1H, exch with D$_2$O); 11.88(s, 1H, exch with D$_2$O). |
| 28 | Exo-(2Z,4E)-5-(5,6-Dichloro-1H-indol-2-yl)-2-methoxy-N-[(8-methyl-8-azabicyclo[3.2.1]oct-3-yl)methyl]-2,4-pentadienamide | N-Me bicyclic exo | H | Me | H | H | H | H | 5Cl | 6Cl | H | 255 | $^1$H NMR(DMSO-d$_6$): 1.10–1.98(m, 9H); 2.13(s, 3H); 2.97(bs, 2H); 3.22(m, 2H); 3.70(s, 3H); 6.57(s, 1H); 6.63(d, 1H); 6.84(d, 1H); 7.16(dd, 1H); 7.51(s, 1H); 7.74(s, 1H); 8.24(t, 1H, exch with D$_2$O); 11.76(s, 1H, exch with D$_2$O). |
| 29 | Endo-(2Z,4E)-5-(5,6-Dichloro-1H-indol-2-yl)-2-methoxy-N-[(8-methyl-8-azabicyclo[3.2.1]oct-3-yl)methyl]-2,4-pentadienamide | N-Me bicyclic endo | H | Me | H | H | H | H | 5Cl | 6Cl | H | 180–198 | $^1$H NMR(DMSO-d$_6$): 1.16–2.03(m, 9H), 2.12(s, 3H); 2.98(bs, 2H); 3.22(m, 2H); 3.70(s, 3H); 6.57(s, 1H); 6.62(d, 1H); 6.84(d, 1H); 7.16(dd, 1H); 7.51(s, 1H); 7.74(s, 1H); 8.24(t, 1H, exch with D$_2$O); 11.75(s, 1H, exch with D$_2$O). |
| 30 | (2Z,4E)-5-(5,6-Dichloro-1H-indol-2-yl)-N-(1,2,3,4-tetrahydro-2,4-dioxopyrimidin-5-yl)-2-methoxy-2,4-pentadienamide | dioxopyrimidinyl | H | Me | H | H | H | H | 5Cl | 6Cl | H | >330 | $^1$H NMR(DMSO-d$_6$): 3.85(s, 3H); 6.61(s, 1H); 6.84(d, 1H); 6.96(d, 1H); 7.21(dd, 1H); 7.52(s, 1H); 7.76(s, 1H); 8.10(s, 1H); 8.69(s, 1H, exch with D$_2$O); 11.25(bm, 2H, exch with D$_2$O); 11.80(s, 1H, exch with D$_2$O). |
| 31 | (2Z,4E)-5-(5,6-Dichloro-1H-indol-2-yl)-2-methoxy-N-(2alpha-hydroxy-8-methyl)-8-azabicyclo[3.2.1]oct-3beta-yl)-2,4-pentadienamide | N-Me bicyclic with OH | H | Me | H | H | H | H | 5Cl | 6Cl | H | 290 | $^1$H NMR(DMSO-d$_6$): 1.53–2.25(m, 6H); 2.58(s, 3H); 3.42–3.85(m, 3H); 3.73(bs, 3H); 3.94(m, 1H); 5.33(bs, 1H, exch with D$_2$O); 6.57(s, 1H); 6.63(d, 1H); 6.85(d, 1H); 7.19(dd, 1H); 7.52(s, 1H); 7.74(s, 1H); 8.02(d, 1H, exch with D$_2$O); 11.82(bs, 1H, exch with D$_2$O). |

-continued

| Ex. No | Name | Rs | Rt | R1 | R2 | R3 | R4 | Ra | R6 | R7 | R8 | MP. (°C) | N.M.R. |
|---|---|---|---|---|---|---|---|---|---|---|---|---|---|
| 32 | (2Z,4E)-5-(5,6-Dichloro-1H-indol-2-yl)-2-methoxy-N-[2-(1-methylethoxy)pyrimidin-5-yl]-2,4-pentadienamide | (5-methylpyrimidin-2-yl with OCH(Me)₂) | H | Me | H | H | H | H | 5Cl | 6Cl | H | 253–254 | $^1$H NMR(DMSO-$d_6$): 1.31(d, 6H); 3.83(s, 3H); 5.16(m, 1H); 6.64(s, 1H); 6.87(d, 1H); 6.98(d, 1H); 7.25(dd, 1H); 7.54(s, 1H); 7.77(s, 1H); 8.87(s, 2H); 10.21(bs, 1H, exch with D$_2$O); 11.82(bs, 1H, exch with D$_2$O) |
| 33 | (2Z,4E)-5-(5,6-Dichloro-1H-indol-2-yl)-2-methoxy-N-[5-(dimethylaminomethyleneamino)pyrimidin-2-yl]-2,4-pentadienamide | (pyrimidin-2-yl with N=CHNMe₂) | H | Me | H | H | H | H | 5Cl | 6Cl | H | 275 | $^1$H NMR(DMSO-$d_6$): 2.95(s, 3H); 3.05(s, 3H); 3.81(s, 3H); 6.62(s, 1H); 6.78(d, 1H); 6.92(d, 1H); 7.23(dd, 1H); 7.53(s, 1H); 7.76(s, 1H); 7.94(s, 1H); 8.33(s, 2H); 10.12(s, 1H, exch with D$_2$O); 11.80(bs, 1H, exch with D$_2$O) |
| 34 | (2Z,4E)-5-(5,6-Dichloro-1H-indol-2-yl)-2-methoxy-N-(8-phenyl-8-azabicyclo[3.2.1]oct-3beta-yl)-2,4-pentadienamide | (8-phenyl-8-azabicyclo[3.2.1]oct-3β-yl) | H | Me | H | H | H | H | 5Cl | 6Cl | H | 233 | $^1$H NMR(DMSO-$d_6$): 1.42–2.08(m, 8H); 3.62(s, 3H); 4.16–4.46(m, 3H); 6.49–6.68(m, 3H); 6.73–6.88(m, 3H); 7.02–7.27(m, 3H); 7.49(s, 1H); 7.74(s, 1H); 7.98(d, 1H, exch with D$_2$O); 11.71(bs, 1H, exch with D$_2$O) |
| 35 | (2Z,4E)-5-(5,6-Dichloro-1H-indol-2-yl)-2-methoxy-N-(2-dimethyl-aminopyrimidin-5-yl)-2,4-pentadienamide | (2-dimethylaminopyrimidin-5-yl) | H | Me | H | H | H | H | 5Cl | 6Cl | H | 299 | $^1$H NMR(DMSO-$d_6$): 3.10(s, 6H); 3.82(s, 3H); 6.62(s, 1H); 6.83(d, 1H); 6.93(d, 1H); 7.24(dd, 1H); 7.53(s, 1H); 7.76(s, 1H); 8.62(s, 2H); 9.93(s, 1H, exch with D$_2$O); 11.80(bs, 1H, exch with D$_2$O) |
| 36 | (2Z,4E)-N-(2-Acetylaminopyrimidin-5-yl)-5-(5,6-dichloro-1H-indol-2-yl)-2-methoxy-2,4-pentadienamide | (2-acetylaminopyrimidin-5-yl) | H | Me | H | H | H | H | 5Cl | 6Cl | H | 307 | $^1$H NMR(DMSO-$d_6$): 2.15(s, 3H); 3.84(s, 3H); 6.64(s, 1H); 6.89(d, 1H); 6.98(d, 1H); 7.25(dd, 1H); 7.54(s, 1H); 7.77(s, 1H); 8.98(s, 2H); 10.29(s, 1H, exch with D$_2$O); 10.54(s, 1H, exch with D$_2$O); 11.82(bs, 1H, exch with D$_2$O) |

| Ex. No | Name | Rs | Rt | R1 | R2 | R3 | R4 | Ra | R6 | R7 | R8 | MP. (°C) | N.M.R. |
|---|---|---|---|---|---|---|---|---|---|---|---|---|---|
| 37 | (2Z,4E)-5-(5,6-Dichloro-1H-indol-2-yl)-N-[2-(1H-imidazol-4-yl)ethyl]-2-methoxy-2,4-pentadienamide | 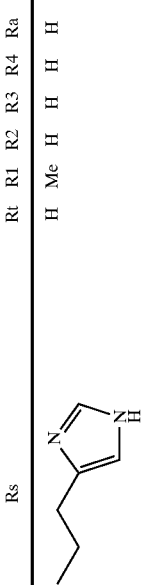 | H | Me | H | H | H | H | 5Cl | 6Cl | H | 140 | ¹H NMR(DMSO-d₆): 2.71(t, 2H); 3.40(q, 2H); 3.70(s, 3H); 6.58(s, 1H); 6.65(d, 1H); 6.85(s, 1H); 6.86(d, 1H); 7.16(dd, 1H); 7.52(s, 1H); 7.61(s, 1H); 7.75(s, 1H); 8.27(t, 1H, exch with D₂O); 11.76(bs, exch with D₂O). |
| 38 | (2Z,4E)-5-(5,6-Dichloro-1H-indol-2-yl)-N-[3-[(tricyclo[3.3.1.1(3,7)]-dec-1-yl)amino]propyl]-2-methoxy-2,6-pentadienamide |  | H | Me | H | H | H | H | 5Cl | 6Cl | H | 220 | ¹H NMR(DMSO-d₆) 1.57(m, 14H); 1.21(m, 3H); 1.92(t, 2H); 1.116(q, 2H); 3.84(s, 3H); 6.58(s, 1H); 6.65(d, 1H); 6.85(d, 1H); 7.17(dd, 1H); 7.51(s, 1H); 7.75(s, 1H); 8.53(t, 1H, exch with D₂O); 11.76(bs, 1H, exch with D₂O). |
| 39 | (2Z,4E)-5-(5,6-Dichloro-1H-indol-2-yl)-2-methoxy-N-(5-pyrimidinyl)-2,4-pentadienamide | 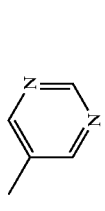 | H | Me | H | H | H | H | 5Cl | 6Cl | H | 293 | ¹H NMR(DMSO-d₆): 3.85(s, 3H); 6.65(s, 1H); 6.92(s, 1H); 7.00(d, 1H); 7.27(dd, 1H); 7.55(s, 1H); 7.78(s, 1H); 8.92(s, 1H); 9.17(s, 2H); 10.41(s, 1H, exch with D₂O); 11.83(bs, 1H, exch with D₂O). |
| 40 | (2Z,4E)-5-(5,6-Dichloro-1H-indol-2-yl)-2-methoxy-N-(2-phenyl-5-pyrimidinyl)-2,4-pentadienamide | 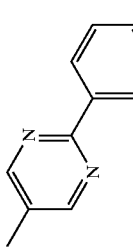 | H | Me | H | H | H | H | 5Cl | 6Cl | H | 299 | ¹H NMR(DMSO-d₆): 3.87(s, 3H); 6.66(s, 1H); 6.94(d, 1H); 7.01(d, 1H); 7.28(dd, 1H); 7.46–7.60(m, 4H); 7.78(s, 1H); 8.36(m, 2H); 9.28(s, 2H); 10.49(s, 1H, exch with D₂O); 11.85(bs, 1H, exch with D₂O). |
| 41 | (2Z,4E)-N-(2-Amino-5-pyrimidinyl)-5-(5,6-dichloro-1H-indol-2-yl)-2-methoxy-2,4-pentadienamide | 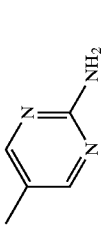 | H | Me | H | H | H | H | 5Cl | 6Cl | H | 305 | ¹H NMR(DMSO-d₆): 11.80(bs, 1H, exch with D₂O); 9.87(s, 1H, exch with D₂O); 8.50(s, 2H); 7.77(s, 1H); 7.54(s, 1H); 7.24(dd, 1H); 6.94(d, 1H); 6.81(d, 1H); 6.63(s, 1H); 6.53(s, 2H, exch with D₂O); 3.81(s, 3H). |

| Ex. No | Name | Rs | Rt | R1 | R2 | R3 | R4 | Ra | R6 | R7 | R8 | MP. (°C.) | N.M.R. |
|---|---|---|---|---|---|---|---|---|---|---|---|---|---|
| 42 | (2Z,4E)-5-[(5,6-Dichloro-1H-indol-2-yl)-N-[3-[4-(4-benzoyl)benzoyl)piperazin-1-yl]propyl]-2-methoxy-2,4-pentadienamide | 4-benzoylbenzoyl-piperazinyl-propyl | H | Me | H | H | H | H | 5Cl | 6Cl | H | 198–200 | ¹H NMR(DMSO-d₆): 11.70(s, 1H); 8.19(t, 1H); 7.80–7.71(m, 5H); 7.70(dd, 1H); 7.60–7.51(m, 5H); 7.17(dd, 1H); 6.84(d, 1H); 6.63(d, 1H); 6.59(s, 1H); 3.71(s, 3H); 3.65(m, 2H); 3.33(m, 2H); 3.22(d, 2H); 2.60–2.30(m, 6H); 1.66(m, 2H). |
| 43 | (2Z,4E)-5-(5,6-Dichloro-1H-indo-2-yl)-N-(2-cyano-5-pyrimidinyl)-2-methoxy-2,4-pentadienamide | 2-cyanopyrimidin-5-yl | H | Me | H | H | H | H | 5Cl | 6Cl | H | 292 | ¹H NMR(DMSO-d₆): 11.84(bs, 1H, exch with D₂O); 10.54(s, 1H, exch with D₂O); 9.15(s, 2H); 7.78(s, 1H); 7.55(s, 1H); 7.27(dd, 1H); 7.01(d, 1H); 6.93(d, 1H); 6.66(s, 1H); 3.85(s, 3H). |
| 44 | (2Z,4E)-5-(1H-indol-2-yl)-N-(3-diethylaminopropyl)-2-methoxy-2,4-pentadienamide | 3-(N,N-diethylamino)propyl | H | Me | H | H | H | H | H | H | H | 134–137 | ¹H NMR(DMSO-d₆): 11.40(s, 1H); 8.23(t br, 1H); 7.48(d, 1H); 7.31(d, 1H); 7.14(dd, 1H); 7.10(dd, 1H); 6.96(dd, 1H); 6.84(d, 1H); 6.66(d, 1H); 6.55(s, 1H); 3.76(s, 3H); 3.25(m, 2H); 2.52(m, 6H); 1.63(m, 2H); 1.00(t, 6H). |
| 45 | (2Z,4E)-5-(1H-indol-2-yl)-2-methoxy-N-(1,2,2,6,6-pentamethyl-piperidin-4-yl)-2,4-pentadienamide | 1,2,2,6,6-pentamethyl-piperidin-4-yl | H | Me | H | H | H | H | H | H | H | 198–201 | ¹H NMR(DMSO-d₆): 11.40(s, 1H); 7.81(d br, 1H); 7.47(d, 1H); 7.32(d, 1H); 7.12(dd, 1H); 7.00(dd, 1H); 6.96(dd, 1H); 6.81(d, 1H); 6.61(d, 1H); 6.55(s, 1H); 4.09(m, 1H); 3.70(s, 3H); 2.20(s, 3H); 1.62(d br, 2H); 1.46(dd br, 2H); 1.09(s, 6H); 1.02(s, 6H). |
| 46 | Ethyl (2Z,4E)-5-(5,6-Dichloro-1H-indol-2-yl)-[(2-methoxy-penta-2,4-dienoyl)amino][2.2.2]octane-2-azabicyclo[2.2.2]octane-2-carboxylate | N-COOEt-azabicyclo[2.2.2]octan-2-yl | H | Me | H | H | H | H | 5Cl | 6Cl | H | 168–170 | ¹H NMR(DMSO-d₆): 1.10–1.28(m, 3H); 1.38–2.23(m, 7H); 3.09–3.59(m, 2H); 3.71 and 3.73(2s, 3H); 3.85–4.12(m, 4H); 6.58(s, 1H); 6.60(d, 1H); 6.85(d, 1H); 7.18(dd, 1H); 7.52(s, 1H); 7.75(s, 1H); 8.17(2d, 1H, exch with D₂O); 11.75(s, broad, 1H, exch with D₂O). |

| Ex. No | Name | Rs | Rt | R1 | R2 | R3 | R4 | Ra | R6 | R7 | R8 | MP. (°C.) | N.M.R. |
|---|---|---|---|---|---|---|---|---|---|---|---|---|---|
| 47 | (2Z,4E)-5-(5,6-Dichloro-1H-indol-2-yl)-2-methoxy-N-(1,2,6-trimethylpiperidin-4-yl)-2,4-pentadienamide | (trimethylpiperidinyl group) | H | Me | H | H | H | H | 5Cl | 6Cl | H | 217 | ¹H NMR(DMSO-d₆): 1.04(d, 6H); 1.32(m, 2H); 1.65(m, 2H); 1.96–2.21(m, 2H); 2.12(s, 3H); 3.70(s, 3H); 3.74(m, 1H); 6.57(s, 1H); 6.60(d, 1H); 6.84(d, 1H); 7.17(dd, 1H); 7.51(s, 1H); 7.75(s, 1H); 7.96(d, 1H, exch with D₂O); 11.75(s, 1H, exch with D₂O) |
| 48 | (2Z,4E)-5-(5,6-Dichloro-1H-indol-2-yl)-2-methoxy-N-[2-[4-(2-methoxyphenyl)piperazin-1-yl]ethyl] 2,4-pentadienamide | (methoxyphenyl-piperazinyl group) | H | Me | H | H | H | H | 5Cl | 6Cl | H | 227–229 | ¹H NMR(DMSO-d₆): 2.45–2.60(m, 6H); 2.96(m, 4H); 3.25–3.35(m, 2H); 3.74(s, 3H); 3.77(s, 3H); 6.59(s, 1H); 6.66(d, 1H); 6.85(d, 1H); 6.84–6.97(m, 4H); 7.18(dd, 1H); 7.51(s, 1H); 7.74(s, 1H); 8.01(t br, 1H); 11.7(s br, 1H). |
| 49 | (2Z,4E)-5-(5,6-Dichloro-1H-indol-2-yl)-N-(8a betaH-5 alpha-methyl-alpha-octahydroindolizin-7alpha-yl)-2-methoxy-2,4-pentadienamide | (octahydroindolizinyl group) | H | Me | H | H | H | H | 5Cl | 6Cl | H | 231 | ¹H NMR(DMSO-d₆): 11.74(s, broad band, 1H exch with D₂O); 8.00(d, 1H exch with D₂O); 7.74(s, H); 7.51(s, 1H); 7.17(dd, 1H); 6.84(d, 1H); 6.60(d, 1H); 6.57(s, 1H); 3.74(m, 1H); 3.70(s, 3H); 3.08(m, 1H); 1.50–2.14(m, 8H); 1.13–1.42(m, 3H); 1.03(d, 3H) |
| 50 | (2Z,4E)-5-(5,6-Dichloro-1H-indol-2-yl)-H-[1-(2-hydroxyethylpiperidin-4-yl)-2-methoxy-2,4-pentadienamide | (hydroxyethylpiperidinyl group) | H | Me | H | H | H | H | 5Cl | 6Cl | H | 218 | ¹H NMR(DMSO-d₆): 11.73(s, broad band, 1H, exch with D₂O); 7.95(d, 1H exch with D₂O); 7.75(s, 1H); 7.51(s, 1H); 7.17(dd, 1H); 6.83(d, 1H); 6.60(d, 1H); 6.57(s, 1H); 4.35(t, 1H exch with D₂O); 3.71(s, 3H); 3.62(m, 1H); 3.48(q, 2H); 2.84(m, 2H); 2.36(t, 2H); 2.00(m, 2H); 1.43–1.74(m, 4H) |

-continued

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 51 | (2Z,4E)-5-(5,6-Dichloro-1H-indol-2-yl)-N-[1-(2,3-dihydroxypropyl)piperidin-4-yl]-2-methoxy-2,4-pentadienamide hydrochloride | (2,6-dimethylpiperidinyl with CH2CH(OH)CH2OH, Me groups) | H | Me | H | H | H | H | 5Cl | 6Cl | H | 275 | ¹H NMR(DMSO-d₆): 11.8(s, broad band, 1H exch with D₂O); 9.49(broad band, 2H, exch with D₂O); 8.29(d, 1H exch with D₂O); 7.75(s, 1H); 7.52(s, 1H); 7.20(dd, 1H ar); 6.85(d, 1H); 6.65(d, 1H); 6.58(s, 1H); 5.53(d, 1H, exch with D₂O); 4.98(m, 1H); 4.36(m, 1H); 3.93(m, 2H); 3.73(s, 3H); 2.87–3.62(m, 6H); 1.94(m, 4H) |
| 52 | Ethyl (2Z,4E)-[(4-[5-(5,6-Dichloro-1H-indol-2-yl)-2-methoxy-penta-2,4-dienoyl]amino]-piperidineacetate | (piperidine with CH2COOEt, Me) | H | Me | H | H | H | H | 5Cl | 6Cl | H | 237 | ¹H NMR(DMSO-d₆): 11.75(s, broad band, 1H, exch with D₂O); 7.99(d, 1H, exch with D₂O); 7.75(s, 1H); 7.52(s, 1H); 7.17(dd, 1H); 6.85(d, 1H); 6.61(d, 1H); 6.58(s, 1H); 4.09(q, 2H); 3.72(s, 3H); 3.65(m, H); 3.19(s, 2H); 2.83(m, 2H); 2.22(m, 2H); 1.46–1.75(m, 4H); 1.19(t, 3H) |
| 53 | (2Z,4E)-5-(5,6-Dichloro-1H-indol-2-yl)-N-[8-(2-acetyloxyethane)-3-azabicyclo[3.2.1]oct-3beta-yl]2-methoxy-2,4-pentadienamide | (azabicyclic with CH2CH2OAc) | H | Me | H | H | H | H | 5Cl | 6Cl | H | 118–120 | ¹H NMR(DMSO-d₆): 11.7(s, broad band 1H exch with D₂O); 7.9(d, 1H, exch with D₂O); 7.75(s, 1H); 7.51(s, 1H); 7.16(dd, 1H); 6.83(d, 1H); 6.60(d, 1H); 6.56(s, 1H); 4.06(m, 3H); 3.69(s, 3H); 3.23(m, H); 2.65(t, 2H); 2.02(s, 3H); 5.81–1.96(m, 8H) |
| 54 | (2Z,4E)-5-(5,6-Dichloro-1H-indol-2-yl)-N-(2a alpha, 4a alpha, 6 alpha, 7a alpha-decahydro-pyrrolo[2.1.5-cd]indolizyn-6-yl)-2-methoxy-2,4-pentadienamide | (decahydropyrroloindolizine) | H | Me | H | H | H | H | 5Cl | 6Cl | H | 226 | ¹H NMR(DMSO-d₆): 11.75(s, broad band, 1H exch with D₂O); 7.91(d, 1H, exch with D₂O); 7.75(s, 1H ar); 7.51(s, 1H ar); 7.17(dd, 1H); 6.84(d, 1H); 6.61(d, 1H); 6.57(s, 1H); 3.73(m, 1H); 3.70(s, 3H); 3.08(m, 3H); 5.26(m, 2H); 1.04–1.81(m, 10H) |
| 55 | (2Z,4E)-5-(5,6-Dichloro-1H-indol-2-yl)-N-(2a beta, 4a alpha, 6 beta, 7a alpha-decahydro-pyrrolo[2.1.5-cd]indolizyn-6-yl)-2-methoxy-2,4-pentadienamide | (decahydropyrroloindolizine) | H | Me | H | H | H | H | 5Cl | 6Cl | H | 238 | ¹H NMR(DMSO-d₆): 11.7(s, broad band, 1H, exch with D₂O); 7.75(s, 1H); 7.62(d, 1H exch with D₂O); 7.52(d, 1H); 7.19(dd, 1H); 6.85(d, 1H); 6.58(s, 1H); 4.04(m, 1H); 3.76(s, 3H); 3.24(m, 3H); 1.00(m, 2H); 1.03–1.85(m, 10H) |

-continued

| Ex. No | Name | Rs | Rt | R1 | R2 | R3 | R4 | Ra | R6 | R7 | R8 | MP. (°C.) | N.M.R. |
|---|---|---|---|---|---|---|---|---|---|---|---|---|---|
| 56 | (2Z,4E)-5-(5,6-Dichloro-1H-indol-2-yl)-N-[8-(2-ethanol)-8-azabicyclo[3.2.1]oct-3beta-yl]-2-methoxy-2,4-pentadienamide | (8-azabicyclooctyl with N-CH₂CH₂OH) | H | Me | H | H | H | H | 5Cl | 6Cl | H | 267–270 | ¹H NMR(DMSO-d₆): 11.79(s, broad band, 1H exch with D₂O); 7.92(d, 1H exch with D₂O); 7.74(s, 1H); 7.52(s, 1H); 7.17(dd, 1H); 6.83(d, 1H); 6.59(d, 1H); 6.57(s, 1H); 4.34(m, 1H, exch with D₂O); 4.03(m, 1H); 3.69(s, 3H); 3.45(m, 2H); 3.21(m, 2H); 2.48(t, 2H); 1.40–1.97(m, 8H) |
| 57 | (2Z,4E)-5-(5,6-Dichloro-1H-indol-2-yl)-2-methoxy-N-(2 alpha, 6 beta 9a alpha)-octahydro-6-methyl-2H-quinolizin-2-yl]-2,4-pentadienamide | (octahydroquinolizinyl with Me) | H | Me | H | H | H | H | 5Cl | 6Cl | H | 200–202 | ¹H NMR(DMSO-d₆): 11.79(s, 1H); 7.74(s, 1H); 7.73(s, 1H); 7.54(s, 1H); 7.13(dd, 1H); 6.84(d, 1H); 6.60(m, 2H); 3.95(s, 1H); 3.73(s, 3H); 3.11(m, 1H); 2.60–2.15(m, 3H); 1.90–1.15(m, 10H); 1.08(d, 3H). |
| 58 | (2Z,4E)-5-(5,6-Dichloro-1H-indol-2-yl)-2-methoxy-N-[1,2,6-trimethylpiperidin-4-yl]-2,4-pentadienamide | (1,2,6-trimethylpiperidin-4-yl) | H | Me | H | H | H | H | 5Cl | 6Cl | H | 214 | ¹H NMR(DMSO-d₆): 11.74(s, broad band, 1H); 7.90(d, 1H); 7.74(s, 1H); 7.51(s, 1H); 7.17(dd, 1H); 6.83(d, 1H); 6.60(d, 1H); 6.56(s, 1H); 4.01(m, 1H); 3.70(s, 3H); 3.05(m, 1H); 2.52(m, 1H); 2.18(s, 3H); 1.85–1.1(m, 4H); 0.96(2d, 6H). |
| 59 | (2Z,4E)-5-(5,6-Dichloro-1H-indol-2-yl)-N-[1-(2-hydroxyethyl)-2,6-dimethylpiperidin-4-yl]-2-methoxy-2,4-pentadienamide | (2,6-dimethylpiperidin-4-yl with N-CH₂CH₂OH) | H | Me | H | H | H | H | 5Cl | 6Cl | H | 150 | ¹H NMR(DMSO-d₆): 11.75(s, broad band, 1H); 7.93(d, 1H); 7.75(s, 1H); 7.51(s, 1H); 7.16(dd, 1H); 6.84(d, 1H); 6.60(d, 1H); 6.57(s, 1H); 4.38(s, broad band, 1H); 3.70(s, 3H); 3.36(t, 2H); 2.80–2.30(m, 5H); 1.77–1.49(m, 2H); 1.38–1.10(m, 2H); 1.05(d, 6H). |
| 60 | (2Z,4E)-5-(5-Bromo-1H-indol-2-yl)-N-2-methoxy-(1,2,2,6,6-pentamethyl-piperidin-4-yl)-2,4-pentadienamide | (1,2,2,6,6-pentamethylpiperidin-4-yl) | H | Me | H | H | H | H | 5Br | H | H | 225–226 | ¹H NMR(DMSO-d₆): 11.61(s, br, 1H); 7.83(d, 1H); 7.68(d, 1H); 7.29(d, 1H); 7.19(dd, 1H); 7.15(dd, 1H); 6.82(d, 1H); 6.59(d, 1H); 6.55(d, 1H); 4.15–4.02(m, 1H); 3.71(s, 3H); 2.18(s, 3H); 1.62(dd, 2H); 1.44(dd, 2H); 1.08(s, 6H); 1.02(s, 6H). |

| Ex. No | Name | Rs | Rt | R1 | R2 | R3 | R4 | Ra | R6 | R7 | R8 | MP. (°C) | N.M.R. |
|---|---|---|---|---|---|---|---|---|---|---|---|---|---|
| 61 | (2Z,4E)-5-(5,6-Dichloro-1H-indol-2-yl)-N-(3-dimethylamino-cyclohexyl)-2-methoxy-2,4-pentadienamide | 3-dimethylamino-cyclohexyl | H | Me | H | H | H | H | 5Cl | 6Cl | H | 200–201 | $^1$H NMR(DMSO-d$_6$): 11.75(s, broad band, 1H); 7.80(s, broad band, 1H); 7.75(s, 1H); 7.51(s, 1H); 7.17(dd, 1H); 6.83(d, 1H); 6.59(d, 1H); 6.57(s 1H); 4.06(m, 1H); 3.71(s, 3H); 2.30–2.20(m, 1H); 2.16(s, 6H); 2.45–1.05(m, 8H). |
| 62 | (2Z,4E)-5-(5,6-Dichloro-1H-indol-2-yl)-N-[3-[2,6-dimethyl-4-(2-pyrimidinyl)piperazin-1-yl]propyl]-2-methoxy-2,4-pentadienamide hydrochloride | [3-[2,6-dimethyl-4-(2-pyrimidinyl)piperazin-1-yl]propyl] | H | Me | H | H | H | H | 5Cl | 6Cl | H | 245 | $^1$H NMR(DMSO-d$_6$): 11.80(s, broad band, 1H); 10.40(s, broad band, 1H); 8.43(d, 2H); 8.39(m, 1H); 7.76(s, 1H); 7.53(s, 2H); 7.19(dd, 1H); 6.87(d, 1H); 6.76(t, 1H); 6.69(d, 1H); 6.59(s, 1H); 4.74(m, 2H); 3.74(s, 3H); 3.50–3.00(m, 8H); 1.82(m, 2H); 1.35(d, 6H). |
| 63 | (2Z,4E)-5-(5,6-Dichloro-1H-indol-2-yl)-2-methoxy-N-[3-[4-(2-methoxyphenyl)-piperazin-1-yl]propyl]2,4-pentadienamide | [3-[4-(2-methoxyphenyl)-piperazin-1-yl]propyl] | H | Me | H | H | H | H | 5Cl | 6Cl | H | 181–182 | $^1$H NMR(DMSO-d$_6$): 11.72(s br, 1H); 8.25(t, 1H); 7.72(s, 1H); 7.50(s, 1H); 7.18(dd, 1H); 6.98–6.81(m, 5H); 6.64(d, 1H); 6.58(s, 1H); 3.76(s, 3H); 3.73(s, 3H); 3.27(d, 2H); 2.99(m, 4H); 2.50(m, 4H); 2.39(t, 2H); 1.73–1.62(m 2H). |
| 64 | (2Z,4E)-5-(5,6-Dichloro-1H-indol-2-yl)-2-methoxy-N-(3-[4-(phenyl)piperazin-1-yl]propyl] 2,4-pentadienamide | (3-[4-(phenyl)piperazin-1-yl]propyl] | H | Me | H | H | H | H | 5Cl | 6Cl | H | 223–225 | $^1$H NMR(DMSO-d$_6$): 11.75(s br, 1H); 8.26(t, 1H); 7.74(s, 1H); 7.51(s, 1H); 7.20(dd, 2H); 7.17(dd, 1H); 6.92(d, 2H); 6.84(d, 1H); 6.79(dd, 1H); 6.65(d, 1H); 6.57(d, 1H); 3.73(s, 3H); 3.26(d, 2H); 3.13(m, 4H); 2.50(m, 4H); 2.39(t, 2H); 1.73–1.62(m, 2H). |

-continued

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 65 | (2Z,4E)-5-(5,6-Dichloro-1H-indol-2-yl)-2-methoxy-4-methyl-N-(1,2,2,6,6-pentamethyl-piperidin-4-yl)-2,4-pentadienamide | 2,2,6,6-tetramethyl-1-methyl-piperidin-4-yl | H | Me | H | Me | H | H | 5Cl | 6Cl | H | 131–132 | $^1$H NMR(DMSO-d$_6$): 11.35(s, br, 1H); 7.89(d, 1H); 7.78(s, 1H); 6.73(s, 1H); 6.62(s, 1H); 6.37(s, 1H); 4.15–4.00(m, 1H); 3.60(s, 3H); 2.29(s, 3H); 2.18(s, 3H); 1.62(dd, 2H); 1.43(dd, 2H); 1.09(s, 6H); 1.02(s, 6H). |
| 66 | (2Z,4E)-5-(5,8-Dichloro-1H,indol-2-yl)-N-[3-(dimethylamino)propyl]-2-methoxy-2,4-pentadienamide | Me-N(Me)-butyl | H | Me | H | H | H | H | 5Cl | 6Cl | H | 181–183 | $^1$H NMR(DMSO-d$_6$): 11.71(s, br, 1H); 8.25(t, 1H); 7.73(s, 1H); 7.51(s, 1H); 7.18(dd, 1H); 6.83(d, 1H); 6.64(d, 1H); 6.58(s, 1H); 3.76(s, 3H); 3.70(s, 3H); 3.20(dt, 2H); 2.24(t, 2H); 2.13(s, 6H); 1.66–1.56(m, 2H). |
| 67 | (2Z,4E)-5-(5,6-Dichloro-1H-indol-2-yl)-N-[(3-dimethylaminophenyl]-2-methoxy-2,4-pentadienamide | Me-N(Me)-(m-tolyl) | H | Me | H | H | H | H | 5Cl | 6Cl | H | 140–141 | $^1$H NMR(DMSO-d$_6$): 11.78(s, br, 1H); 9.70(s, 1H); 7.76(s, 1H); 7.52(s, 1H); 7.23(dd, 1H); 7.20–7.08(m, 3H); 6.91(d, 1H); 6.77(d, 1H); 6.61(s, 1H); 6.48(d br, 1H); 3.81(s, 3H); 2.89(s, 6H). |
| 68 | (2Z,4E)-5-(5,6-Dichloro-1H-indol-2-yl)-N-[3-[-4-(3-chlorophenyl)piperazin-1-yl]propyl]-2-methoxy-2,4-pentadienamide | 4-(3-chlorophenyl)piperazin-1-yl-propyl | H | Me | H | H | H | H | 5Cl | 6Cl | H | 192–193 | $^1$H NMR(DMSO-d$_6$): 11.73(s, br, 1H); 8.24(t, 1H); 7.74(s, 1H); 7.50(s, 1H); 7.20(dd, 2H); 7.16(dd, 1H); 6.95–8.88(m, 2H); 6.83(d, 1H); 6.78(d, 1H); 6.63(d, 1H); 6.58(s, 1H); 3.70(s, 3H); 3.26(dt, 2H); 3.18(m, 4H); 2.50(m, 4H); 2.39(t, 2H); 1.72–1.63(m, 2H). |
| 69 | (2Z,4E)-5-(5,6-Dichloro-1H-indol-2-yl)-N-[3-[-4-(4-chlorophenyl)piperazin-1-yl]propyl]-2-methoxy-2,4-pentadienamide | 4-(4-chlorophenyl)piperazin-1-yl-propyl | H | Me | H | H | H | H | 5Cl | 6Cl | H | 218–219 | $^1$H NMR(DMSO-d$_6$): 11.72(s, br, 1H); 8.23(t, 1H); 7.73(s, 1H); 7.50(s, 1H); 7.21(d, 2H); 7.16(dd, 1H); 6.93(d, 2H); 6.84(d, 1H); 6.64(d, 1H); 6.58(s, 1H); 3.73(s, 3H); 3.24(dt, 2H); 3.11(m, 4H); 2.50(m, 4H); 2.39(t, 2H); 1.71–1.62(m, 2H). |

| Ex. No | Name | Rs | Rt | R1 | R2 | R3 | R4 | Ra | R6 | R7 | R8 | MP. (°C) | N.M.R. |
|---|---|---|---|---|---|---|---|---|---|---|---|---|---|
| 70 | (2Z,4E)-5-(5,6-Dichloro-1H-indol-2-yl)-N-[3-[4-(2-chlorophenyl)piperazin-1-yl]propyl]-2-methoxy-2,4-pentadienamide | 2-chlorophenyl-piperazine-propyl | H | Me | H | H | H | H | 5Cl | 6Cl | H | 193–194 | ¹H NMR(DMSO-d₆): 11.71(s, 1H); 8.23(t, 1H); 7.74(s, 1H); 7.51(s, 1H); 7.40(dd, 1H); 7.29(ddd, 1H); 7.16(dd, 1H); 7.15(dd, 1H); 7.02(ddd, 1H); 6.85(d, 1H); 6.65(d, 1H); 6.59(s, 1H); 3.74(s, 3H); 3.25(d, 1H); 3.00(m, 4H); 2.55(m, 4H); 2.40(t, 2H); 2.22–2.13(m, 2H). |
| 71 | (2Z,4E)-5-(5,6-Dichloro-1H-indol-2-yl)-N-[3-(dibutylamino)propyl]-2-methoxy-2,4-pentadienamide | dibutylamino-propyl | H | Me | H | H | H | H | 5Cl | 6Cl | H | 144–146 | ¹H NMR(DMSO-d₆): 11.72(s br, 1H); 8.18(t, 1H); 7.74(s, 1H); 7.51(s, 1H); 7.17(dd, 1H); 6.84(d, 1H); 6.63(d, 1H); 6.58(s, 1H); 3.72(s, 3H); 3.18(dt, 2H); 2.40–2.31(m, 6H); 1.63–1.54(m, 2H); 1.40–1.21(m, 8H); 0.87(t, 6H). |
| 72 | (2Z,4E)-5-(5,6-Dichloro-1H-indol-2-yl)-N-[3-[4-(2,6-dimethylphenyl)piperazin-1-yl]propyl]-2-methoxy-2,4-pentadienamide | 2,6-dimethylphenyl-piperazine-propyl | H | Me | H | H | H | H | 5Cl | 6Cl | H | 228–230 | ¹H NMR(DMSO-d₆): 11.71(s br, 1H); 8.20(t, 1H); 7.74(s, 1H); 7.52(s, 1H); 7.17(dd, 1H); 6.97–6.89(m, 3H); 6.85(d, 1H); 6.65(d, 1H); 6.58(s, 1H); 3.75(s, 3H); 3.25(d, 2H); 3.02(m, 4H); 2.47(m, 4H); 2.39(t, 2H); 2.27(s, 6H); 1.73–1.63(m, 2H). |
| 73 | (2Z,4E)-5-(5,6-Dichloro-1H-indol-2-yl)-2-methoxy-N-[3-[4-(pyrrolidin-2-one)propyl]-2,4-pentadienamide | pyrrolidin-2-one-propyl | H | Me | H | H | H | H | 5Cl | 6Cl | H | 165–167 | ¹H NMR(DMSO-d₆): 11.79(s br, 1H); 8.14(t, 1H); 7.52(s, 1H); 7.18(dd, 1H); 6.85(d, 1H); 6.66(d, 1H); 6.58(s, 1H); 3.75(s, 3H); 3.34(t, 2H); 3.20(t, 2H); 3.14(dt, 2H); 2.22(t, 2H); 1.97–1.87(m, 2H); 1.69–1.60(m, 2H). |
| 74 | (2Z,4E)-5-(5,6-Dichloro-1H-indol-2-yl)-N-[3-[4-(2-pyrimidinyl)homopiperazin-1-yl]propyl]-2-methoxy-2,4-pentadienamide | 2-pyrimidinyl-homopiperazine-propyl | H | Me | H | H | H | H | 5Cl | 6Cl | H | 220–222 | ¹H NMR(DMSO-d₆): 11.71(s, 1H); 8.32(d, 2H); 8.17(t br, 1H); 7.74(s, 1H); 7.51(s, 1H); 7.16(dd, 1H); 6.84(d, 1H); 6.63(d, 1H); 6.57(s br, 1H); 6.55(dd, 1H); 3.83–3.77(m, 2H); 3.74(t, 2H); 3.72(s, 3H); 3.19(d, 2H); 2.73–2.66(m, 2H); 2.58–2.51(m, 2H); 2.45(t, 2H); 1.88–1.77(m, 2H); 1.67–1.55(m, 2H). |

-continued

| Ex. No | Name | Rs | Rt | R1 | R2 | R3 | R4 | Ra | R6 | R7 | R8 | MP. (° C.) | N.M.R. |
|---|---|---|---|---|---|---|---|---|---|---|---|---|---|
| 75 | (2Z,4E)-5-(5,6-Dichloro-1H-indol-2-yl)-N-[3-[4-(2-pyridyl)piperazin-1-yl]propyl]-2-methoxy-2,4-pentadienamide | 1-(2-pyridyl)-4-propylpiperazine | H | Me | H | H | H | H | 5Cl | 6Cl | H | 219–220 | $^1$H NMR(DMSO-d$_6$): 11.80(s br, 1H); 8.25(t br, 1H); 8.10(dd, 1H); 7.72(s, 1H); 7.51(s, 1H); 7.51(ddd, 1H); 7.19(dd, 1H); 6.82(d, 1H); 6.80(d, 1H); 6.64(d, 1H); 6.61(dd, 1H); 6.58(s, 1H); 3.71(s, 3H); 3.46(m, 4H); 3.23(dt, 2H); 2.46(m, 4H); 2.39(t, 2H); 1.73–1.63(m, 2H). |
| 76 | (2Z,4E)-5-(5,6-Dichloro-1H-indol-2-yl)-2-methoxy-N-[3-[4-(3-methoxyphenyl)-piperazin-1-yl]-propyl] 2,4-pentadienamide | 1-(3-methoxyphenyl)-4-propylpiperazine | H | Me | H | H | H | H | 5Cl | 6Cl | H | 172–173 | $^1$H NMR(DMSO-d$_6$): 11.70(s br, 1H); 8.25(t br, 1H); 7.72(s, 1H); 7.50(s, 1H); 7.16(dd, 1H); 7.10(dd, 1H); 6.84(d, 1H); 6.64(d, 1H); 6.57(s, 1H); 6.52(dd, 1H); 6.44(dd, 1H); 6.36(dd, 1H); 3.72(s, 3H); 3.24(t, 2H); 3.13(m, 4H); 2.50(m, 4H); 2.40(t br, 2H); 1.73–1.64(m, 2H). |
| 77 | (2Z,4E)-5-(5,6-Dichloro-1H-indol-2-yl)-2-methoxy-N-[3-[4-(4-methoxyphenyl)-piperazin-1-yl]propyl] 2,4-pentadienamide | 1-(4-methoxyphenyl)-4-propylpiperazine | H | Me | H | H | H | H | 5Cl | 6Cl | H | 197–199 | $^1$H NMR(DMSO-d$_6$): 11.70(s br, 1H); 8.25(t br, 1H); 7.74(s, 1H); 7.51(s, 1H); 7.16(dd, 1H); 6.88–680(ABq, 4H); 6.84(d, 1H); 6.65(d, 1H); 6.57(s br, 1H); 3.73(s, 3H); 3.67(s, 3H); 3.25(dt, 2H); 3.02(m, 4H); 2.51(m, 4H); 2.39(t, 2H); 1.72–1.63(m, 2H). |

List of Abbreviations Used in the Above Preparations and Examples

| | |
|---|---|
| Florisil | Registered trademark |
| Celite | Registered trade mark for dicalite |
| DMF | Dimethylformamide |
| EI | Electron Impact |
| AcOEt | Ethyl acetate |
| FAB POS | Fast Atom Bombardment/Positive ions detection |
| MS | Mass Spectrum |
| THF | Tetrahydrofuran |
| TSP | ThemoSpray |

Biological Assays

Background. It is known that, upon attachment to bone, an electrogenic $H^+$-adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., Science, 245, 855 (1989)] and than confirmed by Bekker [P. J. Bekker et al., J. Bone Min. Res., 5, 569 (1990)] and Väänänen [K. K. Väänänen et al., J. Cell. Biol., 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin $A_1$, a selective inhibitor of vacuolar $H^+$-ATPases [J. E. Bowman et al., Proc. Natl. Acad. Sci. USA, 85, 7972 (1988)], whilst it was not inhibited by ouabain, an inhibitor of $Na^+/K^+$-ATPases; sodium orthovanadate, an inhibitor of p-ATPases, or by omeprazole or SCH 28080, both of which are inhibitors of gastric $H^+/K^+$-ATPase [J. P. Mattson et al., Acta Physiol. Scand., 146, 253 (1992)].

It is known that specific inhibitors of vacuolar ATPases, such as bafilomycin $A_1$, are able to inhibit bone resorption in osteoclast cultures [K. Sundquist et al., Biochem. Biophys. Res. Commun. 168, 309–313 (1990)]

Inhibition of Proton Transport and v-ATPase Activity in Membrane Vesicles

Preparation of Crude Bone Microsomes from Calcium-Starved Egg-Laying Hens.

Vesicles were prepared from medullar bone obtained from tibiae and femurs of egg-laying hens which were calcium-starved for at least 15 days. Briefly, bone fragments were scraped with a 24 scalpel blade, suspended in 40 ml of isolation medium (0.2 M sucrose, 50 mM KCl, 10 mM Hepes, 1 mM EGTA, 2 mM dithiotheitrol, pH 7.4) and filtered through a 100 µm pore size nylon mesh. The whole procedure was performed at 4° C. After homogenisation in a potter (20 strokes) in 40 ml of isolation medium an initial centrifugation ($6,500 \times g_{max} \times 20$ min) was performed to remove mitochondria and lysosomes. The supernatant was centrifuged at $100,000 \times g_{max}$ for 1 hr and the pellet was collected in 1 ml of isolation medium, divided into 200 µl aliquots, immediately frozen in liquid nitrogen and stored at −80° C. The protein content was determined using a Biorad colourimetric kit according to Bradford [M. Bradford, Anal. Biochem., 72, 248 (1976)]. For the proton transport assay, 5–10 µl of membranes were used.

Purification of osteoclast membranes. 1 ml of crude microsomal vesicles prepared above were applied (about 0.2 ml per tube) on the top of a sucrose step-gradient consisting of 3.5 ml of 15%, 30% and 45% (w/w) sucrose in isolation medium and centrifuged at 280,000 $g_{max}$ for 2 hours (SW 41 Ti rotor). After centrifugation the 30–45% sucrose interfaces were collected, diluted approx. 20-fold in isolation medium and pelletted at 100,000 $g_{max}$ for 1 hour (SW 28 rotor). The pellet was then resuspended in 1 ml of isolation medium, aliquoted and frozen in liquid $N_2$ and stored at −80° C. until used.

Human kidney membranes were obtained from the cortex of a human kidney, frozen immediately after surgery, according to the method reported in the literature for bovine kidney (S. Gluck, J. Biol. Chem., 265, 21957 (1990)).

Proton transport in membrane vesicles was assessed, semi-quantitatively, by measuring the initial slope of fluorescence quench of acridine orange (excitation 490 nm; emission 530) after addition of 5–20 µl of membrane vesicles in 1 ml of buffer containing 0.2 M sucrose, 50 mM KCl, 10 mM Hepes pH 7.4, 1 mM ATP.Na$_2$, 1 mM CDTA, 5 µM valinomycin and 4 µM acridine orange. The reaction was started by addition of 5 mM $MgSO_4$. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin A1. The reaction medium contained 1 mM ATP, 10 mM HEPES-Tris pH 8, 50 mM KCl, 5 uM valinomycin, 5 uM nigericin, 1 mM CDTA-Tris, 100 uM ammonium molybdate, 0.2 M sucrose and membranes (20 ug protein/ml). The reaction was initiated by $MgSO_4$ (8-arm pipette) and stopped, after 30 min, by addition of 4 volumes of the malachite green reagent (96-arm pipette) prepared according to Chan [Anal. Biochem. 157, 375 (1986)]. Absorbance at 650 nm was measured after 2 min using a microplate reader. Results are expressed as µmol (Pi)×mg protein$^{-1}$×hour$^{-1}$ and, for each experiment, represent the mean±sem of triplicates.

Pharmacological Data:

Inhibition of Bafilomycin-Sensitive ATPase in Chicken Osteoclasts

The compounds of the present invention are able to inhibit bafilomycin-sensitive ATPase in chicken osteoclast in a range from 18 nM to 1000 nM. In particular:

| Ex. No | IC$_{50}$ (nM) ATPase assay |
|---|---|
| 1 | 24 |
| 55 | 23 |
| 59 | 24 |
| 61 | 41 |
| 62 | 30 |
| 64 | 67 |
| 68 | 18 |
| 74 | 42 |
| 75 | 30 |

Inhibition of Bone Resorption

In vitro Assays

1) Bone resorption by disaggregated rat osteoclasts can be assessed as described previously in the literature [T. J. Chambers et al., Endocrinology, 1985, 116, 234]. Briefly, osteoclasts were mechanically disaggregated from neonatal rat long bones into Hepes-buffered medium 199 (Flow, UK). The suspension was agitated with a pipette, and the larger fragments were allowed to settle for 30 sec. The cells were then added to two wells of a multiwell dish containing bone slices (each measuring 12 mm$^2$). After 15 min at 37° C. the bone slices were removed, washed in medium 199 and placed in individual wells of a 96-well plate. These were incubated for 24 hrs in a total volume of 2 ml of culture medium, consisting of 10% foetal calf serum in Hanks-buffered MEM, in the presence or absence of drug. The number of osteoclasts and bone resorption were quantified by confocal laser scanning microscopy (CLSM): the bone slices were fixed with 2% glutaraldehyde in 0.2 M cacodylate buffer and the osteoclasts on each bone slice were stained for tartrate-resistant acid phosphatase. After counting the number of large, multinucleated, red-stained cells, the bone slices were immersed in 10% sodium hypochlorite for 5 min to remove cells, washed in distilled water and sputter-coated with gold. The entire surface of each bone slice was then examined in CLSM. The number and the size of the osteoclastic excavations, the plain area and the volume of bone resorbed was recorded. Results were expressed as mean pit number per bone slice, mean pit number per osteoclast, mean area per osteoclast or mean volume per osteoclast.

2) Bone resorption by human osteoclasts can be assessed using a modification of the method above. Briefly, human osteoclasts are purified from human giant cell tumours by negative selection using Pan Human HLA II antibodies in conjunction with Dynal magnetic beads. Osteoclasts are seeded onto bovine bone slices in Hepes-buffered medium 199 (Flow, UK). After 30 minutes, the bone slices are transferred into a 24-well multi-plate (4 slices per well) containing 2 ml/well of medium, consisting of 10% foetal calf serum in D-MEM. One hour later, vehicle (DMSO) or test compounds at different concentrations in DMSO were added and incubation was continued for 47 hours. Bone slices were then treated and analysed as described above for the rat osteoclast assay.

3) Inhibition of PTH-stimulated $^{45}Ca^{2+}$ release from pre-labelled foetal rat long bone. The assay is based on that described by Raisz (*J. Clin. Invest.* 44:103–116, 1965). Time-mated Sprague-Dawley rats were injected subcutaneously with 200 mCi of $^{45}CaCl2$ on the 18th day of gestation. On the following day, the foetuses were removed aseptically and the radii and ulnae were dissected free of adjacent soft tissue and the cartilaginous ends, and then cultured for 24 hr at 37° C. in BGJ medium containing 1 mg/ml BSA. The bones were then transferred to fresh medium containing the test compounds (0.1–50 $\mu$M) with and without PTH (12 nM) and were incubated for an additional 48 hr. The media were collected and the bones extracted to determine the mean % calcium release by scintillation counting. Results were expressed as the % inhibition compared to the amount of calcium released from cultures incubated with PTH alone In vivo Assays Prevention of retinoid-induced hypercalcaemia. The method used was that described by Trechsel et al., (*J. Clin. Invest.* 80:1679–1686, 1987). Briefly, male Sprague-Dawley rats weighing 160–200 g (10 per group) were thyroparathyroidectomised and were treated subcutaneously with the retinoid Ro 13-6298 (30 $\mu$g/day) for three days and this was found to significantly increase blood serum calcium by 4–5 mg/100 ml. For inhibition of this effect, rats were treated simultaneously with test compounds i.v. or p.o. at 0.1–100 mg/kg, or vehicle and blood calcium was measured as described above, before treatment and one day after the last administration. Results were expressed as % inhibition with respect to vehicle-treated animals.

Prevention of bone loss in osteoporosis induced by ovariectomy and immobilisation. Seven groups of 10 Sprague-Dawley rats (200 g) underwent ovariectomy plus neurectomy of the sciatic nerve in the right hind limb, while one group was sham-operated according to the method described by Hayashi et al., (*Bone* 10:25–28, 1989). It was demonstrated that a steady-state was attained in the amount of trabecular bone lost 6–12 weeks after the operations. During a 6-week period, the operated animals received the test compounds (0.1–100 mg/kg p.o. u.i.d.), or vehicle. At the end of this treatment period, the animals were sacrificed and the tibia and femur of the hind limb removed. The tibia wet and dry weight were determined, and the density (displacement of water) and ashes content (total weight, calcium and phosphorous content) also measured. The femur were fixed in 10% formalin, de-mineralised in 5% formic acid and the coronal midshaft and longitudinal section of the distal metaphysis cut and stained with haematoxilin and eosin. Histomorphometric evaluation was made using a semi-automated image analyser (Immagini & Computer, Milan, Italy). In the distal metaphysis, the % trabecular bone area in the secondary spongiosa (which is the trabecular bone 1 mm from the epiphyseal growth plate to about 4 mm towards the midshaft giving a total area of 5 mm$^2$) and the number of trabeculae (according to Parfitt et al., *J. Bone Min. Res.* 2: 595, (1987)) were determined in all animals. In the midshaft, the medullary, cortical (CA) and total (TA) cross-sectional area was measured and the cortical index (CI) determined from the formula CI=CA/TA.

Prevention of bone loss in ovariectomised mature rats. The methodology employed is based on that described by Wronsky et al. [*J. Bone Min. Res.,* 6, 387 (1991)]. The bone loss, prevalently cancellous, occuring after the surgery is monitored by dual emission X-ray absorptiometry (DEXA) measurements of bone mineral density (BMD) of long bones and by HPLC measurements of urinary levels of products of bone collagen breakdown, such as the cross-link residues pyridinoline (PYD), deoxypyridinoline (DPD) and lysine glycosides, i.e. galactosyl-hydroxylysine (GHYL) and glucosyl-galactosyl-hydroxylysine (GGHYL). Groups of 7–10 female Sprague-Dawley rats, about 90 days old and weighing 200–250 g are used. Rats are anesthetised by sodium pentobarbital (35 mg/kg i.v.), laparotomy is performed and ovaries are bilaterally removed. Wounds are adequately disinfected and sutured. A group is sham operated. During a 4-week experimental period, the operated animals receive test compounds in the appropiate vehicle (0.1–100 mg/kg p.o. u.i.d.) or vehicle alone. Twenty-four-hr urine samples are collected for PYD, DPD, GHYL and GGHYL determinations before and 2, 4, 8, 11, 15, 18, 22 and 25 days after surgery. The aliquots of urine are frozen and stored at −20° C. until HPLC analysis.

Before and at the end of the experimental period, the bone metaphyseal mineral densities of left distal femur and proximal tibia were evaluated in vivo using lightly anaesthetised animals. Results are expressed as % of prevention of bone loss versus vehicle treated animals, using the following equation, where BMD indicates the bone mineral density at the end of the experimental period and is expressed as the percent of pre-ovariectomy baseline:

$$\text{Percent prevention} = \frac{\text{BMD(treatment)} - \text{BMD(vehicle)}}{\text{BMD(sham)} - \text{BMD(vehicle)}} \times 100$$

Biological Data for Compound of Example 1

| | |
|---|---|
| Human Osteoclast Resorption Assay | $IC_{50} = 3.4$ nM |
| Human Kidney ATPase assay | $IC_{50} = 363$ nM |
| Protection of bone loss in ovariectomised mature rats at 10 mg/kg p.o. | 76% |

Other Therapeutic Utilities:

The activity of the compounds of the invention for the other utilities mentioned herein may be determined by according to the following methods which are incorprated herein:

1. Antitumor activity may be determined according to the methods disclosed in published International Application, Publication number 93/18652; in particular the screen employed, experimental details and bibliography of M. R. Boyd et al., *Status of the NCI preclinical antitumor drug discovery screen; principles and practices of Oncology*, 3, issue 10, October 1989, Lippincott.
2. Antiviral activity may be assessed using the in vitro assays reported by H. Ochiai et al., *Antiviral Research*, 27, 425–430 (1995) or by C. Serra et al., *Pharmacol. Res.*, 29, 359 (1994). Anti-HIV activity can be assessed as reported in the literature, for example by S. Velásquez et al., *J. Med. Chem.*, 38, 1641–1649 (1995)
3. Antiulcer activity may be assessed in vivo using the methods reported in the literature, for example, as described by C. J. Pfeiffer, *Peptic Ulcer*, C. J. Pfeiffer Ed., Munksgaard Publ., Copenaghen, 1971. In vitro assays for inhibition of vacuolization induced by *Helicobacter pylori* are described, for example, by E. Papini et al., *FEMS Microbiol Lett.*, 113, 155–160 (1993)
4. Usefulness in treating Alzheimer's disease may be determined using models in vitro such as inhibition of amiloyd-β production as descrided in the literature by J. Knops et al., *J. Biol. Chem.*, 270, 2419–2422 (1995) or by models in vivo: such as the transgenic mouse model overexpressing human APP reported by D. Games et al., *Nature*, 373, 523–527 (1995).
5. Immunosuppressant activity can be assessed as reported in the literature, for example by M.-K. Hu et al., *J. Med. Chem.*, 38, 4164–4170 (1995)
6. Antilipidemic activity can be assessed as reported in the literature, for example by E. A. L. Biessen et al., *J. Med. Chem.* 38, 1846–1852 (1995). Antiatherosclerotic activity may be assessed by using animal models of atherosclerosis, such as the atherosclerotic rabbit model, which are reported in the literature, for example by R. J. Lee et al., *J. Pharm. Exp. Ther.*, 184, 105–112 (1973).
7. Angiostatic activity may be assessed using the methods reported in the literature, for example as described by T. Ishii et al., *J. Antibiot.*, 48, 12 (1995).

What is claimed is:
1. A compound of formula (I):

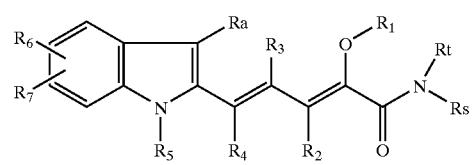

selected from the group of compounds in the following table, wherein the substituents $R_s$, $R_t$, $R_1$, $R_2$, $R_3$, $R_4$, $R_5$, $R_6$, $R_7$ and $R_8$ have the meanings indicated therein:

| Ex. No. | Name | Rs |
|---|---|---|
| 1a | (2Z,4E)-5-(5,6-Dichloro-1H-indol-2-yl)-2-methoxy-N-(1,2,2,6,6-pentamethyl-piperidin-4-yl)-2,4-pentadienamide | (2,2,6,6-tetramethyl-1-methyl-piperidin-4-yl) |
| 1b | (2E,4E)-5-(5,6-Dichloro-1H-indol-2-yl)-2-methoxy-N-(1,2,2,6,6-pentamethyl-piperidin-4-yl)-2,4-pentadienamide | (2,2,6,6-tetramethyl-1-methyl-piperidin-4-yl) |
| 1c | (2Z,4Z)-5-(5,6-Dichloro-1H-indol-2-yl)-2-methoxy-N-(1,2,2,6,6-pentamethyl-piperidin-4-yl)-2,4-pentadienamide | (2,2,6,6-tetramethyl-1-methyl-piperidin-4-yl) |
| 2 | (2Z,4E)-5-(5,6-Dichloro-1H-indol-2-yl)-2-methoxy-N-(6-ethoxy-pyridin-3-yl)-2,4-pentadienamide | 6-ethoxy-pyridin-3-yl ($OC_2H_5$) |
| 3 | (2Z,4E)-N-(5-Chloropyridin-2-yl)-5-(5,6-dichloro-1H-indol-3-yl)-2-methoxy-2,4-pentadienamide | 5-chloro-pyridin-2-yl (Cl) |
| 4 | (2Z,4E)-5-(5,6-Dichloro-1H-indol-2-yl)-2-methoxy-N-[(2,4-dimethoxy)-pyridin-3-yl]-2,4-pentadienamide | 2,4-dimethoxy-pyridin-3-yl (OMe, MeO) |
| 5 | (2Z,4E)-5-(5,6-Dichloro-1H-indol-2-yl)-2-methoxy-N-(2-methoxy-pyrimidin-5-yl)-2,4-pentadienamide | 2-methoxy-pyrimidin-5-yl (OMe) |
| 6 | (2Z,4E)-5-(5,6-Dichloro-1H-indol-2-yl)-2-methoxy-N-(5-methoxy-pyridin-3-yl)-2,4-pentadienamide | 5-methoxy-pyridin-3-yl (OMe) |

-continued

| | | |
|---|---|---|
| 7 | (2Z,4E)-5-(5,6-Dichloro-1H-indol-2-yl)-2-methoxy-N-(3-(4-benzoyl-piperazin-1-yl)propyl]-2,4-pentadienamide | |
| 8 | (2Z,4E)-5-(5,6-Dichloro-1H-indol-2-yl)-N-[6-(2-hydroxyethoxy)-pyridin-3-yl]-2-methoxy-2,4-pentadienamide | |
| 9 | (2Z,4E)-5-(5,6-Dichloro-1H-indol-2-yl)-2-methoxy-N-(2-pyridyloxy-5-pyridyl)-2,4-pentadienamide hydrochloride | |
| 10 | (S,2Z,4E)-5-(5,6-Dichloroindol-2-yl)-N-[2-(1-carbethoxy)-ethoxy-5-pyridyl]-2-methoxy-2,4-pentadienamide | |
| 11 | (S,2Z,4E)-5-(5,6-Dichloroindol-2-yl)-N-[2-(1-carbethoxy)ethoxy-5-pyridyl]-2-methoxy-2,4-pentadienamide | |
| 12 | (2Z,4E)-5-(5,6-Dichloro-1H-indol-2-yl)-2-methoxy-N-[6-(1-methyl-ethoxy)pyridin-3-yl]-2,4-pentadienamide | |
| 13 | (2Z,4E)-5-(5,6-Dichloro-1H-indol-2-yl)-2-methoxy-N-(6-dimethyl-aminopyridin-3-yl)-2,4-pentadienamide | |
| 14 | (2Z,4E)-5-(5,6-Dichloro-1H-indol-2-yl)-2-methoxy-N-(1-azabicyclo-[3.3.1]nonan-4 beta-yl)-2,4-pentadienamide | |
| 15 | (2Z,4E)-5-(5,6-Dichloro-1H-indol-2-yl)-2-methoxy-N-(9-methyl-9-azabicyclo[3.3.1]nonan-3 alpha-yl)-2,4-pentadienamide | |
| 16 | (2Z,4E)5,6-Dichloro-1H-indol-2-yl)-2-methoxy-N-(8-methyl-8-aza-bicyclo[3.2.1]oct-3alpha-yl)-2,4-pentadienamide | |
| 17 | (2Z,4E)-5-(5,6-Dichloro-1H-indol-2-yl)-N-[6-(2-methoxyethoxy)-pyridin-3-yl]-2-methoxy-2,4-pentadienamide | |
| 18 | (2Z,4E)-5-[2-(1-Carboxymethyl-5,6-dichloro)indolyl]-2-methoxy-N-[5-(2-methoxy-pyridinyl]-2,4-pentadienamidehydrochloride | |
| 19 | (2Z,4E)-5-(5,6-Dichloro-1H-indol-2-yl)-N-[6-(2-diethylaminoethoxy)-pyrid-3-yl]-2-methoxy-2,4-pentadienamide hydrochloride | |
| 20 | (2Z,4E)-5-(5,6-Dichloro-1H-indol-2-yl)-N-(1-methylethyl-6-oxo-pyridin-3-yl)-2-methoxy-2,4-pentadienamide | |
| 21 | (2Z,4E)-5-(1H-Indol-2-yl)-2-methoxy-N-[4-(2,2,5,6-tetramethyl)-piperidinyl]-2,4-pentadienamide hydrochloride | |
| 22 | (2Z,4E)-5-(5,6-Dichloro-3-ethyl-1H-indol-2-yl)-2-methoxy-N-[4-(2,2,6,6-tetramethyl)piperidinyl]-2,4-pentadienamide hydrochloride | |
| 23 | (2Z,4E)-5-(5,6-Dichloro-1H-indol-2-yl)-N-[6-(2-dimethylaminoethyl-amino)-pyrid-3-yl]-2-methoxy-2,4-pentadienamide hydrochloride | |
| 24 | (2Z,4E)-5-[(5,6-Dichloro-1H-indol-2-yl)-2-methoxy-N-[3-piperazin-1-yl)-propyl]-2,4-pentadienamide | |
| 25 | (2Z,4E)-5-(5,6-Dichloro-1-methylindol-2-yl)-2-methoxy-N-[4-(2,2,6,6-tetramethyl)piperidinyl]-2,4-pentadienamide | |
| 26 | (2Z,4E)-5-(5-Trifluoromethylindol-2-yl)-2-methoxy-N-[4-(2,2,6,6-tetramethyl)piperidinyl]-2,4-pentadienamide hydrochloride | |
| 27 | (2Z,4E)-5-(5,6-Dichloro-1H-indol-2-yl)-2-methoxy-N-(3,7-dimethyl-3,7-diazabicyclo[3.3.1]nonan-9-yl)-2,4-pentadienamide | |

-continued

| | | |
|---|---|---|
| 28 | Exo-(2Z,4E)-5-(5,6-Dichloro-1H-indol-2-yl)-2-methoxy-N-[(8-methyl-8-azabicyclo[3.2.1]oct-3-yl)methyl]-2,4-pentadienamide | |
| 29 | Endo-(2Z,4E)-5-(5,6-Dichloro-1H-indol-2-yl)-2-methoxy-N-[(8-methyl-8-azabicyclo[3.2.1]oct-3-yl)methyl]-2,4-pentadienamide | |
| 30 | (2Z,4E)-5-(5,6-Dichloro-1H-indol-2-yl)-N-(1,2,3,4-tetrahydro-2,4-dioxopyrimidin-5-yl)-2-methoxy-2,4-pentadienamide | |
| 31 | (2Z,4E)-5-(5,6-Dichloro-1H-indol-2-yl)-2-methoxy-N-(2alpha-hydroxy-8-methyl)-8-azabicyclo[3.2.1]oct-3beta-yl)-2,4-pentadienamide | |
| 32 | (2Z,4E)-5-(5,6-Dichloro-1H-indol-2-yl)-2-methoxy-N-[2-(1-methylethoxy)-pyrimidin-5-yl]-2,4-pentadienamide | |
| 33 | (2Z,4E)-5-(5,6-Dichloro-1H-indol-2-yl)-2-methoxy-N-[5-(dimethylaminomethyleneamino)-pyrimidin-2-yl]-2,4-pentadienamide | |
| 34 | (2Z,4E)-5-(5,6-Dichloro-1H-indol-2-yl)-2-methoxy-N-(8-phenyl-8-azabicyclo-[3.2.1]oct-3beta-yl)-2,4-pentadienamide | |
| 35 | (2Z,4E)-5-(5,6-Dichloro-1H-indol-2-yl)-2-methoxy-N-(2-dimethylaminopyrimidin-5-yl)-2,4-pentadienamide | |
| 36 | (2Z,4E)-N-(2-Acetylaminopyrimidin-5-yl)-5-(5,6-dichloro-1H-indol-2-yl)-2-methoxy-2,4-pentadienamide | |
| 37 | (2Z,4E)-5-(5,6-Dichloro-1H-indol-2-yl)-N-[2-(1H-imidazol-4-yl)ethyl]-2-methoxy-2,4-pentadienamide | |
| 38 | (2Z,4E)-5-(5,6-Dichloro-1H-indol-2-yl)-N-[3-[(tricyclo[3.3.1.1.(3,7)]-dec-1-yl)amino]propyl]-2-methoxy-2,6-pentadienamide | |
| 39 | (2Z,4E)-5-(5,6-Dichloro-1H-indol-2-yl)-2-methoxy-N-(5-pyrimidinyl)-2,4-pentadienamide | |
| 40 | (2Z,4E)-5-(5,6-Dichloro-1H-indol-2-yl)-2-methoxy-N-(2-phenyl-5-pyrimidinyl)-2,4-pentadienamide | |
| 41 | (2Z,4E)-N-(2-Amino-5-pyrimidinyl)-5-(5,6-dichloro-1H-indol-2-yl)-2-methoxy-2,4-pentadienamide | |
| 42 | (2Z,4E)-5-[(5,6-Dichloro-1H-indol-2-yl)-N-[3-[4-(4-benzoyl)benzoylpiperazin-1-yl]propyl]-2-methoxy-2,4-pentadienamide | |
| 43 | (2Z,4E)-5-(5,6-Dichloro-1H-indo-2-yl)-N-(2-cyano-5-pyrimidinyl)-2-methoxy-2,4-pentadienamide | |
| 44 | (2Z,4E)-5-(1H-indol-2-yl)-N-(3-diethylaminopropyl)-2-methoxy-2,4-pentadienamide | |
| 45 | (2Z,4E)-5-(1H-indol-2-yl)-2-methoxy-N-(1,2,2,6,6-pentamethylpiperidin-4-yl)-2,4-pentadienamide | |
| 46 | Ethyl (2Z,4E)-5-(5,6-Dichloro-1H-indol-2-yl)-[(2-methoxy-penta-2,4-dienoyl)amino]-2-azabicyclo[2.2.2]octane-2-carboxylate | |
| 47 | (2Z,4E)-5-(5,6-Dichloro-1H-indol-2-yl)-2-methoxy-N-(1,2,6-trimethylpiperidin-4-yl)-2,4-pentadienamide | |

| Ex. No. | Rt | R1 | R2 | R3 | R4 | Ra | R6 | R7 | R8 |
|---|---|---|---|---|---|---|---|---|---|
| 1a | H | Me | H | Me | H | H | 5Cl | 6Cl | H |
| 1b | H | Me | H | Me | H | H | 5Cl | 6Cl | H |
| 1c | H | Me | H | Me | H | H | 5Cl | 6Cl | H |
| 2 | H | Me | H | H | H | H | 5Cl | 6Cl | H |
| 3 | H | Me | H | H | H | H | 5Cl | 6Cl | H |
| 4 | H | Me | H | H | H | H | 5Cl | 6Cl | H |

-continued

| | | | | | | | | | |
|---|---|---|---|---|---|---|---|---|---|
| 5 | H | Me | H | H | H | H | 5Cl | 6Cl | H |
| 6 | H | Me | H | H | H | H | 5Cl | 6Cl | H |
| 7 | H | Me | H | H | H | H | 5Cl | 6Cl | H |
| 8 | H | Me | H | H | H | H | 5Cl | 6Cl | H |
| 9 | H | Me | H | H | H | H | 5Cl | 6Cl | H |
| 10 | H | Me | H | H | H | H | 5Cl | 6Cl | H |
| 11 | H | Me | H | H | H | H | 5Cl | 6Cl | H |
| 12 | H | Me | H | H | H | H | 5Cl | 6Cl | H |
| 13 | H | Me | H | H | H | H | 5Cl | 6Cl | H |
| 14 | H | Me | H | H | H | H | 5Cl | 6Cl | H |
| 15 | H | Me | H | H | H | H | 5Cl | 6Cl | H |
| 16 | H | Me | H | H | H | H | 5Cl | 6Cl | H |
| 17 | H | Me | H | H | H | H | 5Cl | 6Cl | H |
| 18 | H | Me | H | H | H | H | 5Cl | 6Cl | CH2—COOH |
| 19 | H | Me | H | H | H | H | 5Cl | 6Cl | H |
| 20 | H | Me | H | H | H | H | 5Cl | 6Cl | H |
| 21 | H | Me | H | H | H | H | H | H | H |
| 22 | H | Me | H | H | H | Et | 5Cl | 6Cl | H |
| 23 | H | Me | H | H | H | H | 5Cl | 6Cl | H |
| 24 | H | Me | H | H | H | H | 5Cl | 6Cl | H |
| 25 | H | Me | H | H | H | H | 5Cl | 6Cl | H |
| 26 | H | Me | H | H | H | H | 5CF$_3$ | H | H |
| 27 | H | Me | H | H | H | H | 5Cl | 6Cl | H |
| 28 | H | Me | H | H | H | H | 5Cl | 6Cl | H |
| 29 | H | Me | H | H | H | H | 5Cl | 6Cl | H |
| 30 | H | Me | H | H | H | H | 5Cl | 6Cl | H |
| 31 | H | Me | H | H | H | H | 5Cl | 6Cl | H |
| 32 | H | Me | H | H | H | H | 5Cl | 6Cl | H |
| 33 | H | Me | H | H | H | H | 5Cl | 6Cl | H |
| 34 | H | Me | H | H | H | H | 5Cl | 6Cl | H |
| 35 | H | Me | H | H | H | H | 5Cl | 6Cl | H |
| 36 | H | Me | H | H | H | H | 5Cl | 6Cl | H |
| 37 | H | Me | H | H | H | H | 5Cl | 6Cl | H |
| 38 | H | Me | H | H | H | H | 5Cl | 6Cl | H |
| 39 | H | Me | H | H | H | H | 5Cl | 6Cl | H |
| 40 | H | Me | H | H | H | H | 5Cl | 6Cl | H |
| 41 | H | Me | H | H | H | H | 5Cl | 6Cl | H |
| 42 | H | Me | H | H | H | H | 5Cl | 6Cl | H |
| 43 | H | Me | H | H | H | H | 5Cl | 6Cl | H |
| 44 | H | Me | H | H | H | H | H | H | H |
| 45 | H | Me | H | H | H | H | H | H | H |
| 46 | H | Me | H | H | H | H | 5Cl | 6Cl | H |
| 47 | H | Me | H | H | H | H | 5Cl | 6Cl | H | or a salt thereof, or a solvate thereof.

2. A process for the preparation of a compound of formula (I) as described in claim 1, which process comprises reacting a compound of formula (II):

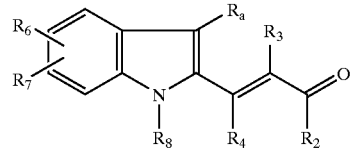

wherein Ra, $R_2$, $R_3$, $R_4$, $R_6$, $R_7$ and $R_8$ are as defined in relation to formula (I), with a reagent capable of converting a moiety of formula

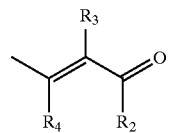

into a moiety of the formula (a):

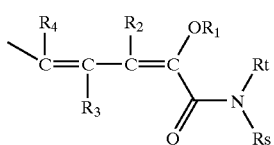

wherein $R_s$, Rt, $R_1$, $R_2$, $R_3$ and $R_4$ are as defined in relation to formula (I), and thereafter, as necessary, carrying out one or more of the following reactions:
 (i) converting one compound of formula (I) into another compound of formula (I);
 (ii) removing any protecting group;
 (iii) preparing a salt or a solvate of the compound so formed.

3. A pharmaceutical composition comprising a compound according to claim 1, and a pharmaceutically acceptable carrier therefor.

4. A method for the treatment of osteoporosis in a mammal which method comprises the administration of a non-toxic, pharmaceutically effective amount of a compound according to claim 1.

* * * * *